(12) United States Patent
Zhang et al.

(10) Patent No.: US 9,987,228 B2
(45) Date of Patent: Jun. 5, 2018

(54) METHOD FOR PRODUCING POROUS PARTICLE

(71) Applicant: National Institute for Materials Science, Ibaraki (JP)

(72) Inventors: Shaoling Zhang, Ibaraki (JP); Kohsaku Kawakami, Ibaraki (JP); Katsuhiko Ariga, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 0 days. days.

(21) Appl. No.: 15/527,204

(22) PCT Filed: Nov. 16, 2015

(86) PCT No.: PCT/JP2015/082087
§ 371 (c)(1),
(2) Date: May 16, 2017

(87) PCT Pub. No.: WO2016/080336
PCT Pub. Date: May 26, 2016

(65) Prior Publication Data
US 2017/0319483 A1 Nov. 9, 2017

(30) Foreign Application Priority Data
Nov. 18, 2014 (JP) ................. 2014-233671

(51) Int. Cl.
| A61K 9/127 | (2006.01) |
| A61K 9/19 | (2006.01) |
| A61K 47/24 | (2006.01) |
| A61K 47/10 | (2017.01) |
| A61K 47/06 | (2006.01) |
| F26B 5/06 | (2006.01) |

(52) U.S. Cl.
CPC .............. *A61K 9/1274* (2013.01); *A61K 9/19* (2013.01); *A61K 47/06* (2013.01); *A61K 47/10* (2013.01); *A61K 47/24* (2013.01); *F26B 5/06* (2013.01)

(58) Field of Classification Search
None
See application file for complete search history.

(56) References Cited

U.S. PATENT DOCUMENTS

| 4,950,432 A | 8/1990 | Mehta et al. |
| 5,178,875 A | 1/1993 | Lenk et al. |
| 2005/0025822 A1* | 2/2005 | Wong .............. A61K 9/0078 424/450 |
| 2005/0129774 A1 | 6/2005 | Morein et al. |
| 2006/0057206 A1 | 3/2006 | Wong et al. |
| 2009/0280181 A1 | 11/2009 | Slager |
| 2009/0324743 A1* | 12/2009 | Carter .............. A61K 9/0078 424/649 |
| 2011/0020225 A1 | 1/2011 | Chung et al. |
| 2014/0088025 A1* | 3/2014 | Cesco-Cancian .... A61K 38/395 514/21.4 |

FOREIGN PATENT DOCUMENTS

| JP | 58135804 A | 8/1983 |
| JP | 03500650 A | 2/1991 |
| JP | 06509547 A | 10/1994 |
| JP | 2005103319 A | 4/2005 |
| JP | 2005533751 A | 11/2005 |
| JP | 2008510000 A | 4/2008 |
| JP | 2010535885 A | 11/2010 |
| JP | 2011520813 A | 7/2011 |

OTHER PUBLICATIONS

JN Israelachvili, S Marcelja, RG Horn. "Physical Principles of Membrane Organization." Quarterly Reviews of Biophysics, vol. 13(2), 1980, pp. 121-200. (Year: 1980).*
Li et al., "Mesoporous Silica Nanoparticles in Biomedical Applications", Chem. Soc. Rev. 41, 2590-2605 (2012).
Wu et al., "Design and Preparation of Porous Polymers", Chem. Rev. 112, 3959-4015, (2012).
Mellaerts et al., "Increasing the Oral Bioavilability of the Poorly Water Soluble Drug Itraconazole with Ordered Mesoporous Silca", Eur. J. Pharm. Biopharm, 69, 223-230 (2008).
Nandiyanto et al., "Progress in Developing Spray-Drying Methods for the Production of Controlled Morphology Particles: From the Nanometer to Submicrometer Size Ranges", Adv. Powder Technol., 22, 1-19, (2011).
Chow et al., "Particle Engineering for Pulmonary Drug Delivery", Pharm. Res., 24, 411-437 (2007).
Chen et al., "Scaffold Design for Tissue Engineering", Macromol. Biosci., 2, 67-77 (2002).
Qian et al., "Controlled Freezing and Freeze Drying: A Versatile Route for Porous and Micro-/Nano-Structured Materials", J. Chem. Technol. Biotechnol, 86, 172-184 (2010).
Teagarden et al., "Practical Aspects of Lyophilization using Non-aqueous Co-Solvent Systems", Eur.J. Pharm. Sci., 15, 115-133 (2002).
Hara et al., "Novel Fractionation Method for Soy Phospholipid Classes", The Journal of the Faculty of Science and Technology, Seikei University, vol. 44, No. 2, 65-73 (2007).
Handbook of Pharmaceutical Excipients, 1st Print, Tokyo: Yakuji Nippo Ltd., Translated and edited by Japan Pharmaceutical Excipients Council, revised edition, pps. 1063-1066 ( 2007).
Kawakami et al., "Mesoporous Phospholipid Particle as a Novel Drug Delivery Plafform", 1st European Conference on Pharmaceutics Abstract Apr. 13-14, 2015, Reims, France.

(Continued)

Primary Examiner — Isaac Shomer
(74) Attorney, Agent, or Firm — Hoffmann & Baron, LLP

(57) ABSTRACT

A method for producing porous particles includes (1) a step of preparing a solution of an amphiphilic substance by dissolving the amphiphilic substance in a mixed solvent capable of being freeze-dried, (2) a step of producing a precipitate containing the amphiphilic substance by cooling the solution obtained in step (1) to a temperature equal to or less than a phase separation temperature of the solution, and thereafter holding the solution at the temperature, and (3) a step of producing porous particles by freeze-drying the solution containing the precipitate obtained in the step (2).

15 Claims, 16 Drawing Sheets

(56) References Cited

OTHER PUBLICATIONS

Kawakami et al., "Mesoporous Phospholipid Particles: A Novel Drug Delivery Platform" 2015 Controlled Release Society Annual Meeting & Exposition Abstracts, Jul. 26-29, Edinburgh, Scotland.
Zhang et al., "Totally Phospholipidic Mesoporous Particles", Journal of Physical Chemistry C, 119, 7255-7263 (2015).
Kohsaku Kawakami, Bio-Inspired Nanoarchitectonics for Early and Patient-Oriented Medical Treatment, MANA International Symposium, Abstract, pp. 1-3, (2015).
NIMS Press Release, "Mesoporous Particles for the Development for Drug Delivery System Safe to Human Bodies", pp. 1-3 (2015).
International Search Report for corresponding PCT Application No. PCT/JP2015/082087, pp. 1-4, Feb. 16, 2016.
Kawakami et al., "Development of a New DDS Platform Carrier: Porous Solid Particles Composed Only of Phospholipids", The 31st Annual Meeting of the Japan Society of Drug Delivery System Abstract, p. 1, Jul. 2-3, 2015, Tokyo, Japan.

* cited by examiner

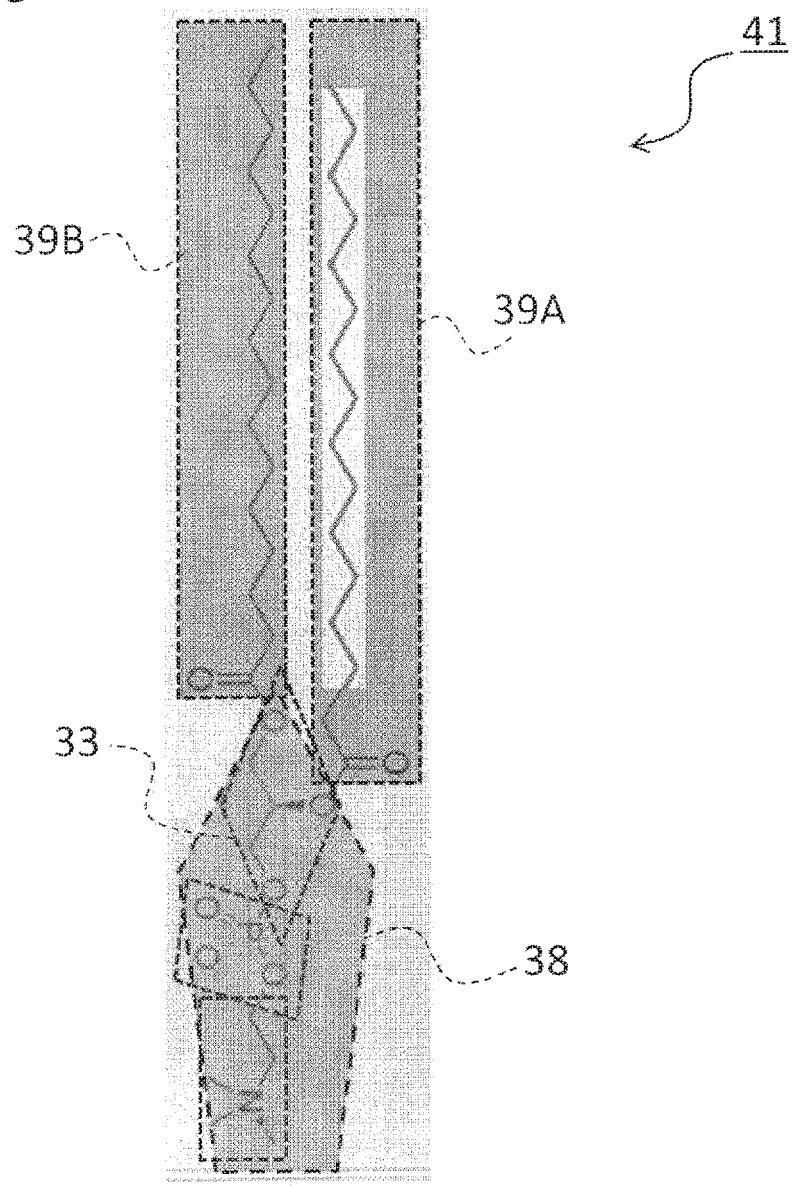

METHOD FOR PRODUCING POROUS PARTICLE

CROSS-REFERENCE TO RELATED APPLICATIONS

This application is a U.S. National Phase Application of International Application No. PCT/JP2015/082087 filed on Nov. 16, 2015 and asserts priority to Japanese Application No. 2014-233671 filed on Nov. 18, 2014, all of which are hereby incorporated by reference in their entirety.

TECHNICAL FIELD

The present invention relates to a method for producing a porous particle, and in particular to a method including phase separation of a solution containing an amphiphilic substance and freeze-drying.

Priority is claimed on Japanese Patent Application No. 2014-233671, filed on Nov. 18, 2014, the content of which is incorporated herein by reference.

BACKGROUND ART

Various porous particles are developed and a potential of a drug delivery system (DDS) as a drug carrier is studied (PTLs 1, 2, and 3). In PTL 1, a porous material excellent in releasing property of a non-steroidal anti-inflammatory compound is provided. In PTL 2, a porous material that functions as a carrier of a drug and drug-containing nanoparticles is disclosed and improvement in oral absorbability of the drug is achieved by improving dissolution. In a case where the porous material is used as a carrier for these low molecule drugs, the objective thereof is dissolution assistance. In PTL 3, porous particles are used as a drug carrier in gene therapy. Stabilization of gene drug and effective intracellular delivery are achieved. The porous particles composed mainly of an inorganic material and/or a carbon material are hard and do not decompose rapidly in a living body, and if the porous particles are present for a long period of time, there is a possibility of adversely affecting the living body. Porous particles using a polymer material are developed (PTLs 4 and 5), but it takes time to decompose the porous particles and impurities such as monomers remain, so that there is a possibility that biological safety problems occur. PTL 4 relates to water-insoluble porous particles of a biocompatible substance and a production method thereof. PTL 5 relates to porous polymer particles on which charged molecules are immobilized and a production method thereof.

NPL 1 is a review article on medical applications of porous silica particles. The use of silica related materials as a porous material is described.

NPL 2 is a review article on preparation of a porous material using a polymer compound. NPL 2 specializes in using polymer compounds.

NPL 3 is a document which confirmed that indomethacin was encapsulated in porous silica, the dissolution of the drug was improved, and the oral absorbability in an animal was improved. The Porous particles are used as a material for improving dissolution.

NPL 4 is a review article on shape control of organic material particles using spray drying. A porous material with an organic compound is disclosed. A method of forming porous particles by removing spray dried particles containing a template by heating or dissolving is disclosed. The pore size is mainly submicron, which is very large, is disclosed.

NPL 5 is a review article on a method of preparing microparticles for pulmonary administration of pharmaceutical products. A method for preparing porous particles by an organic material is disclosed. It is disclosed that porous particles can be obtained by adding a material that vaporizes during spray drying. The pore size is mainly submicron, which is very large, is disclosed.

NPL 6 discloses that a porous material directed to use in regenerative medicine can be prepared by freeze-drying.

CITATION LIST

Patent Literature

[PTL 1] Published Japanese Translation No. 2005-533751 of the PCT International Publication
[PTL 2] Published Japanese Translation No. 2008-510000 of the PCT International Publication
[PTL 3] Published Japanese Translation No. 2011-520813 of the PCT International Publication
[PTL 4] Japanese Unexamined Patent Application, First Publication No. 2005-103319
[PTL 5] Published Japanese Translation No. 2010-535885 of the PCT International Publication

Non-Patent Literature

[NPL 1] Chem. Soc. Rev. 41, 2590-2605 (2012)
[NPL 2] Chem. Rev. 112, 3959-4015 (2012)
[NPL 3] Eur. J. Pharm. Biopharm. 69, 223-230 (2008)
[NPL 4] Adv. Powder Technol. 22, 1-19 (2011)
[NPL 5] Pharm. Res. 24, 411-437 (2007)
[NPL 6] Macromol. Biosci. 2, 67-77 (2002)

SUMMARY OF INVENTION

Technical Problem

An object of the present invention is to provide a method for producing porous particles which are highly biologically safe and can contain guest molecules, particularly drug molecules, and to provide the porous particles obtained by the method and the porous particles containing guest molecules.

Solution to Problem

As a result of various studies to achieve the above object, when a mixed solvent system containing amphiphilic substances is cooled and freeze-dried, surprisingly, it has been found that solid particles having substantially uniform particle sizes can be obtained, the particles have pores with a size of nano order or larger, and the particles can carry various substances, so that the present invention is completed.

That is, the present invention is as follows.

[1] A method for producing porous particles includes (1) a step of preparing a solution of an amphiphilic substance by dissolving the amphiphilic substance in a mixed solvent capable of being freeze-dried, (2) a step of producing a precipitate containing the amphiphilic substance by cooling the solution obtained in step (1) to a temperature equal to or less than a phase separation temperature of the solution, and thereafter holding the solution at the temperature, and (3) a step of producing porous particles by freeze-drying the solution containing the precipitate obtained in the step (2).

[2] The above method in which the porous particles have a lamellar structure.

[3] The above method in which the amphiphilic substance is a phospholipid.

[4] The above method in which the phospholipid is at least one selected from the group consisting of phosphatidylcholine, phosphatidylglycerol, phosphatidylethanolamine, phosphatidylserine, phosphatidylinositol, phosphatidic acid, sphingomyelin, and ceramide.

[5] The above method in which the phospholipid is a phospholipid of natural origin.

[6] The above method in which the phospholipid of natural origin is hydrogenated soybean lecithin or hydrogenated egg yolk lecithin.

[7] The above method in which the amphiphilic substance is at least one selected from the group consisting of dicetyl phosphate, dihexadecyl phosphate, dioctadecyl dimethyl ammonium salt, and stearylamine.

[8] The above method in which the mixed solvent is a mixed solvent of two or more solvents selected from the group consisting of water, t-butanol, cyclohexane, dioxane, dimethylsulfoxide, diethylamine, acetic acid, and t-amyl alcohol.

[9] The above method in which the mixed solvent further contains at least one solvent selected from the group consisting of methanol, ethanol, propanol, isopropanol, butanol, hexane, heptane, octane, isooctane, nonane, decane, dodecane, ethers, acetonitrile, acetone, chloroform, dichloromethane, dimethylformamide, dimethylacetamide, N-methylpyrrolidone, isopentane, methylamine, ethylamine, isobutane, and ethylene oxide.

[10] The above method in which in step (1), a biocompatible substance is further dissolved.

[11] The above method further includes (4) a step of mixing porous particles with a biocompatible substance.

[12] The above method in which the biocompatible substance is a medicine.

[13] The above method in which the medicine is at least one selected from the group consisting of a low molecular medicine, a peptide medicine, an antibody medicine, and a nucleic acid medicine.

[14] The above method in which the biocompatible substance is at least one selected from the group consisting of a stabilizer, a humectant, a thickener, and an excipient.

[15] The above method in which the volume average particles size of the porous particles is 100 nm or more and 50 μm or less.

Advantageous Effects of Invention

According to the production method of the present invention described above, for example, in a case where the phospholipid is used, porous particles having substantially uniform particle sizes of 100 nm or more and 50 μm or less can be obtained. Each step of the production method is easy to industrialize and does not require any special substance. The pore size of the obtained porous particles is distributed from nano order to submicron, various guest molecules can be incorporated into the main body and micropores, and the release rate can be changed, so that it is extremely useful as a sustained release carrier or the like.

BRIEF DESCRIPTION OF DRAWINGS

FIG. 3 is an enlarged view of phospholipid which is an example of an amphiphilic molecule 41.

DESCRIPTION OF EMBODIMENTS

[Porous Particles]

First, porous particles obtained by the method of the present invention will be described.

Figure 1A:
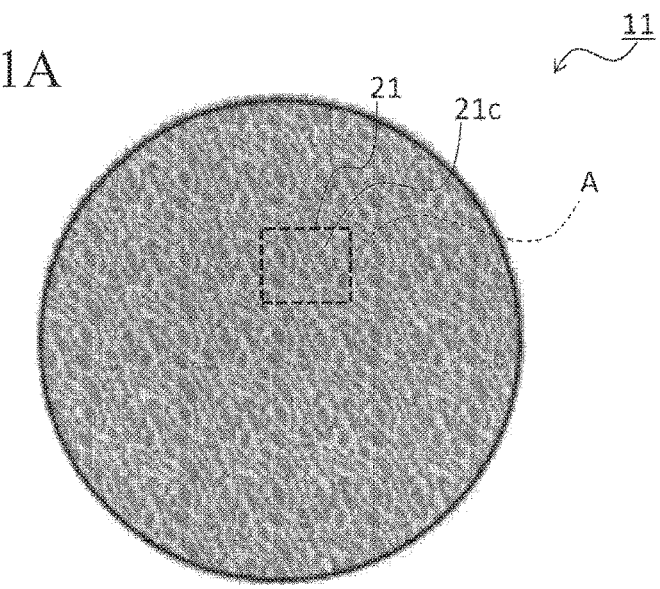
FIG. 1A is a general view of a schematic view illustrating an example of porous particles according to an embodiment of the present invention.
Figure 1B:
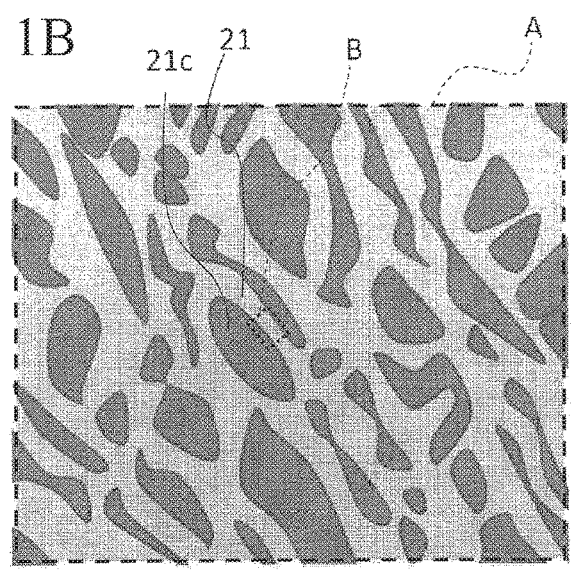
FIG. 1B is an enlarged view of a portion A of FIG. 1A.
Figure 1C:
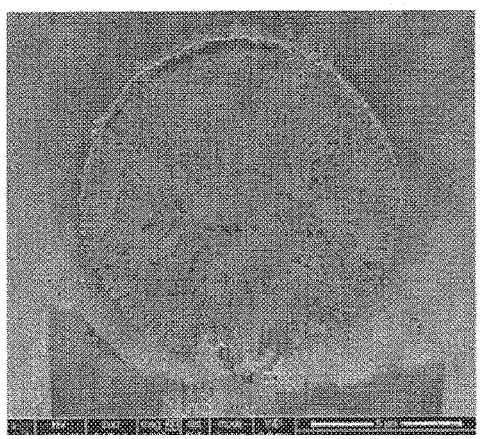
FIG. 1C is a scanning electron microscope (SEM) photograph of a cross section of one example of the porous particles in FIG. 1A.

FIG. 1A is a schematic view illustrating an example of porous particles and is a general view, FIG. 1B is an enlarged view of a portion A of FIG. 1A, and FIG. 1C is a cross section SEM photograph.

The porous particle 11 illustrated in FIG. 1A is substantially spherical. However, without being limited thereto, it may be in various forms such as an oval sphere or the like.

In a case where use for an oral formulation is assumed, it is preferable that the volume average particle size is 50 μm or less in order to ensure the surface area. In addition, in a case where pulmonary administration is assumed, since effective inhalation treatment is expected by setting the aerodynamic diameter to several μm, it is desirable that the volume average particle size is 20 μm or less. The lower limit of the particle size is not particularly limited, but it is desirable that it is 100 nm or more in order to facilitate handling. In addition, according to the method of the present invention, a narrow particle size distribution can be realized.

As illustrated in FIG. 1B, the porous particle 11 has a portion 21 formed of an amphiphilic substance, for example, phospholipid, and a pore 21c. The pore 21c extends from the surface to the inside as illustrated in a cross section photograph (FIG. 1C).

Figure 2A:
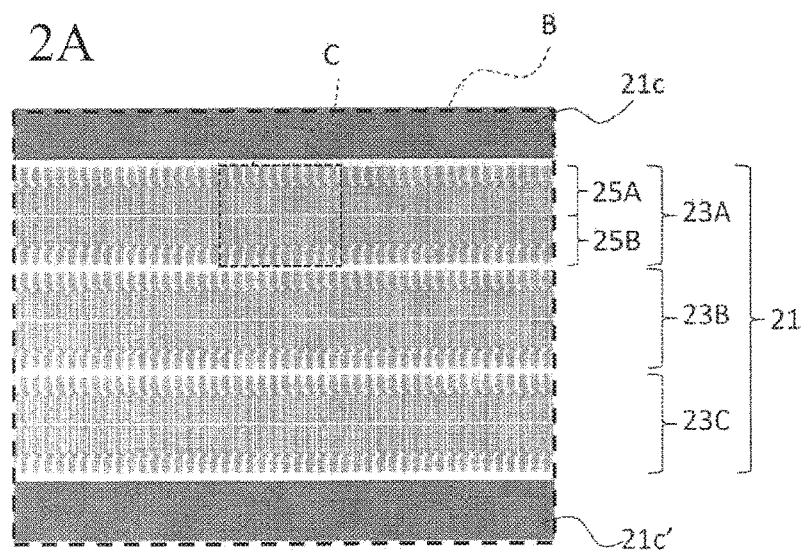
FIG. 2A is an enlarged view of a portion B in FIG. 1B
Figure 2B:
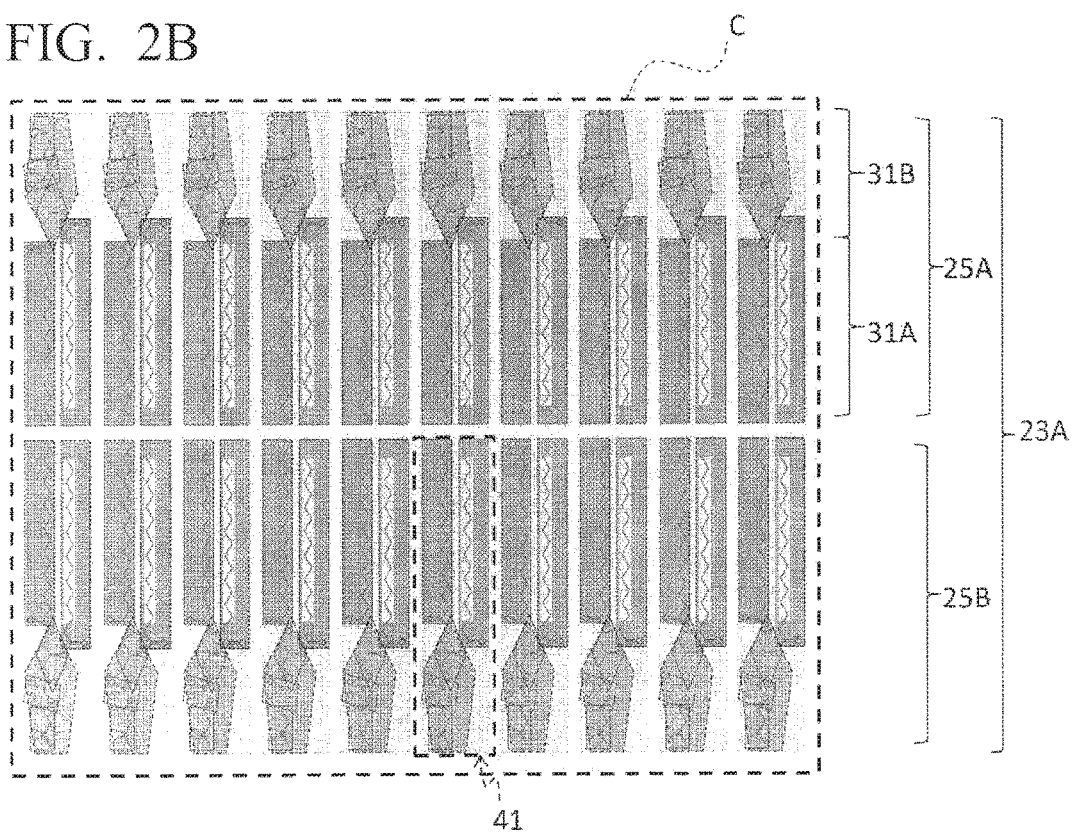
FIG. 2B is an enlarged view of a portion C in FIG. 2A.

FIG. 2A is an enlarged view of a portion B in FIG. 1B, and FIG. 2B is an enlarged view of a portion C in FIG. 2A.

As illustrated in FIG. 2A, lipid bilayer membranes 23A, 23B, and 23C are laminated between two pores 21c and 21c' to form a lamellar structure. However, the actual number of layers is arbitrary, and is not limited to three layers.

As illustrated in FIG. 2B, the lipid bilayer membrane 23A is configured in a state where a lipid layer 25A is gathered with the other lipid layer 25B by attaching hydrophobic groups 31A. A plurality of lipid bilayer membranes gather to form a lamellar structure.

FIG. 3 is an enlarged view of phospholipid, having a hydrophilic group 38 and two hydrophobic groups 39A and 39B bonded to the hydrophilic group 38.

The hydrophobic groups 39A and 39B are preferably saturated hydrocarbon chains of C12 or more and C18 or less, and are not preferably unsaturated hydrocarbon chains. Since the phospholipid having an unsaturated hydrocarbon chain has a low frozen phase glass transition temperature, it is difficult to set freeze-drying conditions that can maintain the particle structure.

The two hydrophobic groups 39A and 39B may be the same as or different from each other.

Examples of the fatty acid having a saturated alkyl group of C12 or more and C18 or less include myristic acid, palmitic acid, stearic acid, and the like.

The hydrophilic group 38 has a linking group 33 bonded to the hydrophobic groups 39A and 39B by an ether bond.

The linking group 33 is a glycerol residue. For example, when a fatty acid is ester-bonded to C1 and C2 positions of glycerin and a phosphate is ester-bonded to a C3 position, it becomes phosphatidic acid.

[Method for Producing Porous Particles]

Next, a method for producing porous particles of the present invention will be described.

The method for producing porous particles according to an embodiment of the present invention includes (1) a step of preparing a solution of an amphiphilic substance, (2) a step of producing a precipitate, and (3) a freeze-drying step.

(1) Step of Preparing Solution of Amphiphilic Substance

In this step, the amphiphilic substance is dissolved in a mixed solvent capable of being freeze-dried. In the present invention, the amphiphilic substance is a substance having a hydrophobic group and a hydrophilic group in the molecule, and is preferably biocompatible. Examples of such amphiphilic substances include natural amphiphilic substances such as the phospholipids, ceramides, and the like described above, synthetic amphipathic substances such as dicetyl phosphate, dihexadecyl phosphate, dioctadecyl dimethyl ammonium salt, stearyl amine, and the like, and those in which the hydrophilic groups of these are modified with molecules for improving the interaction with guest drugs or the ability to deliver drugs to an internal target site such as polyethylene glycol and membrane permeable peptides.

As the phospholipid, it is desirable that a hydrophobic chain portion thereof has only a saturated hydrocarbon chain. Examples of the phospholipid include Phosphatidylcholine (lecithin), Phosphatidylglycerol, Phosphatidylethanolamine, Phosphatidylserine, Phosphatidylinositol, Sphingomyelin, and the like.

Lipid mixtures of natural origin may be used as the phospholipids, and examples of the phospholipids include hydrogenated soybean lecithin and hydrogenated egg yolk lecithin. The hydrogenated soybean lecithin is composed mainly of, for example, 87 wt % of distearylphosphatidylcholine and 13 wt % of dipalmitoylphosphatidylcholine. The phosphatidyl derivative and the lipid having an unsaturated hydrocarbon chain may be mixed with the phospholipid to the extent that the porous structure does not collapse. In addition, cholesterol may be added to the extent that the porous structure does not collapse.

Examples of the ceramides include animal ceramide, vegetable ceramide, bioceramide, and synthetic ceramide. The phosphatidyl derivative and the lipid having an unsaturated hydrocarbon chain may be mixed with the ceramides to the extent that the porous structure does not collapse. In addition, cholesterol may be added to the extent that the porous structure does not collapse.

Examples of the mixed solvent capable of being freeze-dried include solvents obtained by mixing two or more solvents selected from water, t-butanol, t-amyl alcohol, cyclohexane, dioxane, dimethylsulfoxide, diethylamine, and acetic acid. Among these solvents, it is preferable to use a solvent obtained by mixing two or more solvents selected from the group consisting of water, t-butanol, cyclohexane and dioxane. The mixed solvent is used in combination and quantitative ratio such that phase separation occurs by cooling in the presence of the amphiphilic substance to be used.

At least one solvent selected from the group consisting of methanol, ethanol, propanol, isopropanol, n-butanol, isobutane, isopentane, hexane, heptane, octane, isooctane, nonane, decane, dodecane, ethers, acetonitrile, acetone, chloroform, dichloromethane, dimethylsulfoxide, dimethylformamide, dimethylacetamide, ethylamine, propylamine, N-methyl pyrrolidone may be further mixed with the mixed solvent.

The method of dissolution is not particularly limited, but a mixed solvent is first prepared, an amphiphilic substance is added thereto, and the dissolution is performed by a normal method using a stirrer or the like. Alternatively, the amphiphilic substance may be dissolved in one solvent, and another solvent may be added to the obtained solution and mixed. When dissolving, it may be heated. In a case where the phospholipid is dissolved in a mixed solvent of t-butanol:cyclohexane=1:2, it is preferable to heat to approximately 50° C. In this manner, it is possible to dissolve the phospholipid having a high concentration of 1 wt % or more, without causing decomposition by heating.

(2) Step of Producing Precipitate

The solution obtained in step (1) is cooled to a temperature equal to or less than a phase separation temperature of the solution, and thereafter held at the temperature to produce a precipitate containing the amphiphilic substance. The temperature at which phase separation occurs depends on at least three component systems of at least two solvents and the amphipathic substance. The cooling means is not particularly limited and may be performed in a freeze dryer. The cooling rate is not particularly limited, but it is preferable to cool relatively rapidly, and the cooling is performed at 0.1° C./min or more. It may be stirred during cooling. Although it is possible to produce the precipitate even if it is held at the phase separation temperature, it is cooled to preferably 1° C. or less, and to more preferably 5° C. or less from the phase separation temperature. Next, it is held at the temperature to produce the precipitate containing the amphipathic substance. For example, in a case where the phospholipid is used, a spherical precipitate containing the phospholipid is produced.

For example, in a case where 6 wt % of hydrogenated soybean lecithin is contained, the phase separation temperature of the t-butanol:cyclohexane=1:2 solution is approximately 18° C. A spherical precipitate containing lecithin of lamellar structure can be generated at a temperature lower than this, and at a temperature that does not freeze, for example, at 4° C.

A retention time is preferably adjusted, depending on the amphipathic substance and the solvent system. For example, in the case of a system of phospholipid and t-butanol:cyclohexane=1:2, it is preferably 5 hours or more and 4 days or less. In approximately several hours, the precipitate may not be formed uniformly in some cases. Conversely, if it is over 4 days, an aggregate will be formed.

(3) Freeze-Drying Step

Next, the solution containing the precipitate obtained in the step (2) is freeze-dried. The freezing temperature is, for example, −20° C. or less, preferably −40° C. or less. Cooling may be performed with liquid nitrogen or in a vacuum freeze dryer.

Prior to freezing, the supernatant liquid may be removed by decantation or the like.

The freeze-drying time is not particularly limited, but it is preferable to set it over half a day. The freeze-drying temperature is, for example, between −40° C. and 40° C., and preferably between −20° C. and 25° C. In the final step of freeze-drying, the residual solvent may be distilled off by heating. The temperature is preferably 50° C. or less and the time is preferably 5 hours or less, but is not limited thereto.

As a freeze drying method, a spray freeze drying method may be used. In this manner, the porous particles are obtained.

[Porous Particles Containing Guest Molecules]

The porous particles can carry any substance (hereinafter referred to as "guest molecules") as a carrier.

Figure 4:
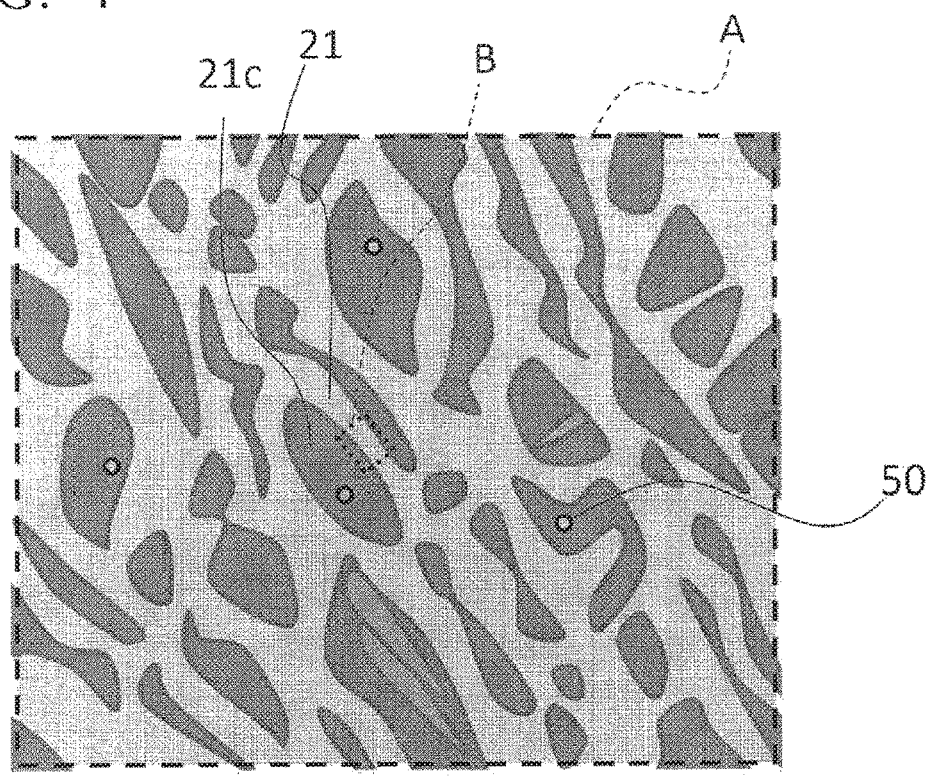
FIG. 4 is a schematic diagram illustrating an example of the porous particles containing guest molecules according to an embodiment of the present invention.
Figure 5:
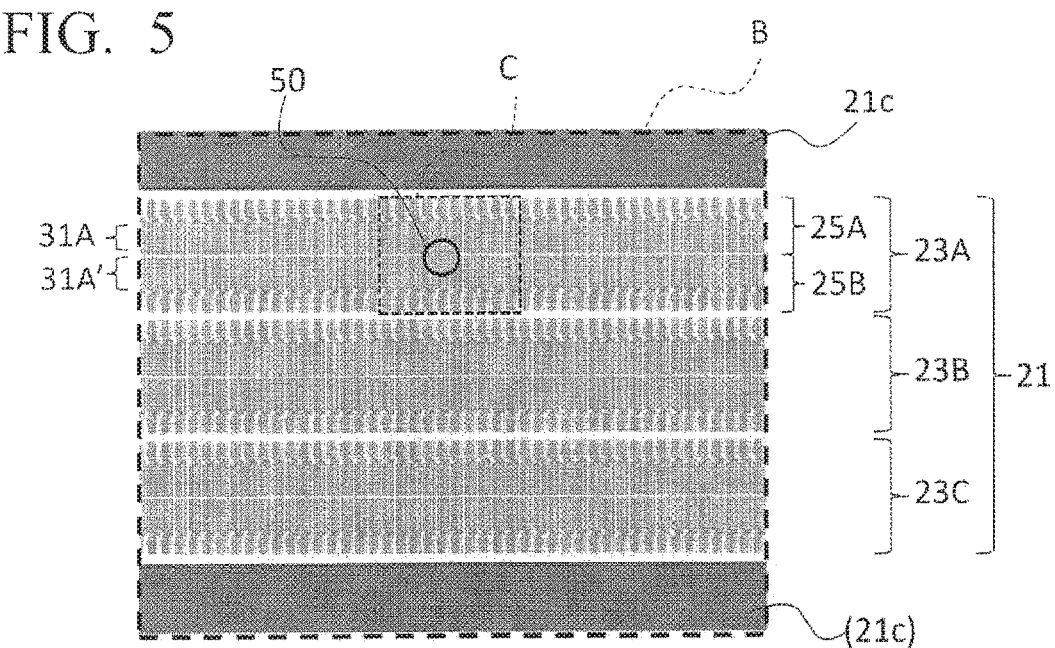
FIG. 5 is a schematic diagram illustrating an example of the porous particles containing the guest molecules according to an embodiment of the present invention.
Figure 6:
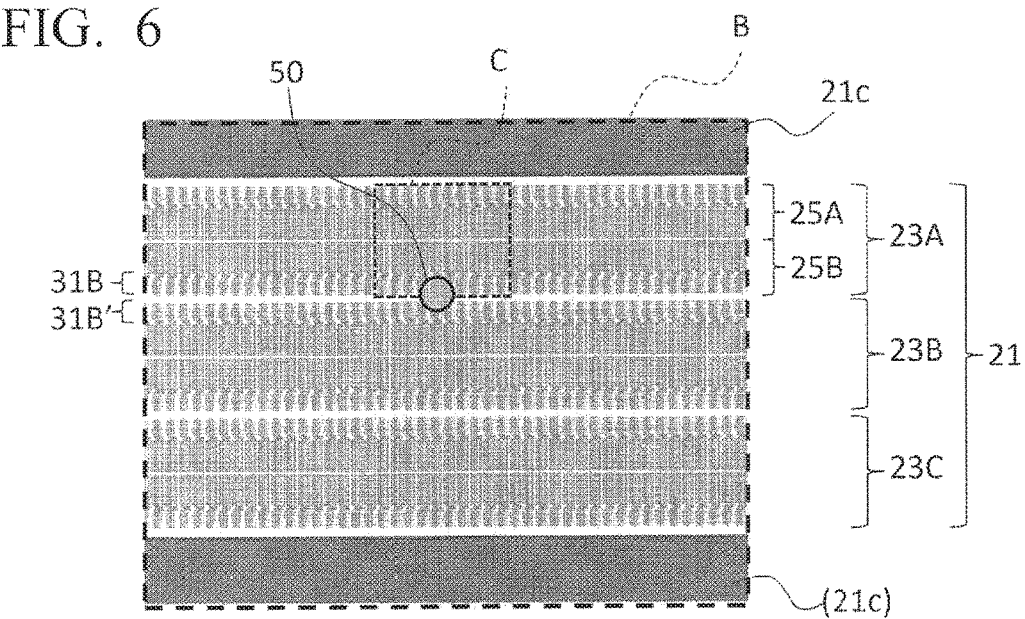
FIG. 6 is a schematic diagram illustrating an example of the porous particles containing the guest molecules according to an embodiment of the present invention.

FIGS. 4 to 6 are schematic diagrams illustrating an example of the porous particles containing the guest molecules. The porous particles containing the guest molecules are substantially composed of the porous particles 11 (FIG. 1) and the guest molecules 50.

The guest molecules 50 may be carried on the surface of the porous particles 11, in the pore, in any portion within the lamellar structure.

In FIG. 4, the guest molecules 50 are incorporated in the pore 21c of the porous particles 11.

In FIG. 5, the guest molecules 50 are incorporated in hydrophobic layers 31A and 31A' of the porous particles 11. That is, the guest molecules 50 are incorporated in the lipid bilayer membrane 23A.

In FIG. 6, the guest molecules 50 are incorporated between hydrophilic layers 31B and 31B' of the porous particles 11. That is, the guest molecules 50 are incorporated between the lipid bilayer membranes 23A and 23B.

A preferred guest molecule 50 is a drug, or other biocompatible substance. As the drug to be incorporated in the lipid bilayer membrane as illustrated in FIG. 5, a hydrophobic low molecular drug including steroids or fat soluble vitamins can be assumed. As illustrated in FIG. 6, examples of the drugs to be incorporated between the lipid bilayer membranes include hydrophilic drugs such as water-soluble low molecular medicines represented by antibiotics and the like, peptide medicine, antibody medicine, nucleic acid medicine and the like. As the water-soluble low molecular medicine, antibiotics can be included. In any case, it may be alone, two or more kinds of drugs may be contained, or a hydrophilic drug and a hydrophobic drug may be simultaneously incorporated.

Examples of other biocompatible substances include conventional pharmaceuticals, cosmetics, and food additives such as stabilizers, humectants, thickeners, and excipients.

Examples of the stabilizer include an antioxidant such as vitamin C or a preservative such as paraben. Examples of the humectant include polyhydric alcohols such as glycerin, propylene glycol, butylene glycol, sorbitol, and the like, water-soluble polymers such as hyaluronic acid, chondroitin sulfate, collagen, gelatin, elastin, keratin, and the like, and hydrolysates thereof, and low molecular compounds such as amino acids and urea. Examples of the thickener include polysaccharides including celluloses, polyvinyl derivatives or synthetic polymers for thickeners. Examples of excipients include saccharides or water-soluble polymers.

In the step (1), the drug and other biocompatible substance may be dissolved in the mixed solvent with the amphiphilic substance or may be mixed as the step (4) mechanically with the porous particles obtained in the step (3).

The content of the guest molecules 50 is preferably adjusted according to the type of the guest molecules, but it is preferably 50 wt % or less, and more preferably 30 wt % or less with respect to the weight of the porous particle.

If the porous particles containing the guest molecules come into contact with a medium having a low guest molecule concentration, for example, digestive tract fluid, the guest molecule can be gradually released from the porous particles containing the guest molecules by a concentration gradient.

The guest molecules are included both within the pores and between the lamellar structures, so that the release rate can be controlled. In addition, hydrophobic guest molecules are included in the hydrophobic layer and hydrophilic guest molecules are included between the hydrophilic layers, so that it is possible to release these while respectively changing the release start time.

APPLICATION EXAMPLES

Hereinafter, the present invention will be described with reference to application examples, but the present invention is not limited to these application examples.
(Production of Porous Particles)

Application Example 1-1

Phospholipids (hydrogenated soybean lecithin manufactured by NOF Corporation) were dissolved in a mixed solvent (mixed solvent of t-butanol:cyclohexane=1:2) to prepare a phospholipid solution (9.6 wt % hydrogenated soybean lecithin solution).

Next, the phospholipid solution was cooled to 0° C. by cooling with ice and the phases were separated, and thereafter held at 0° C. for 24 hours to produce a precipitate.

Next, the precipitate was frozen with liquid nitrogen to produce a frozen product.

Next, the frozen product was held in a freeze-drier, held at −20° C. for half a day under reduced pressure, thereafter the temperature was raised to room temperature and freeze-dried for 1 day, so that the porous particles of Application Example 1-1 were produced.

Figure 7:
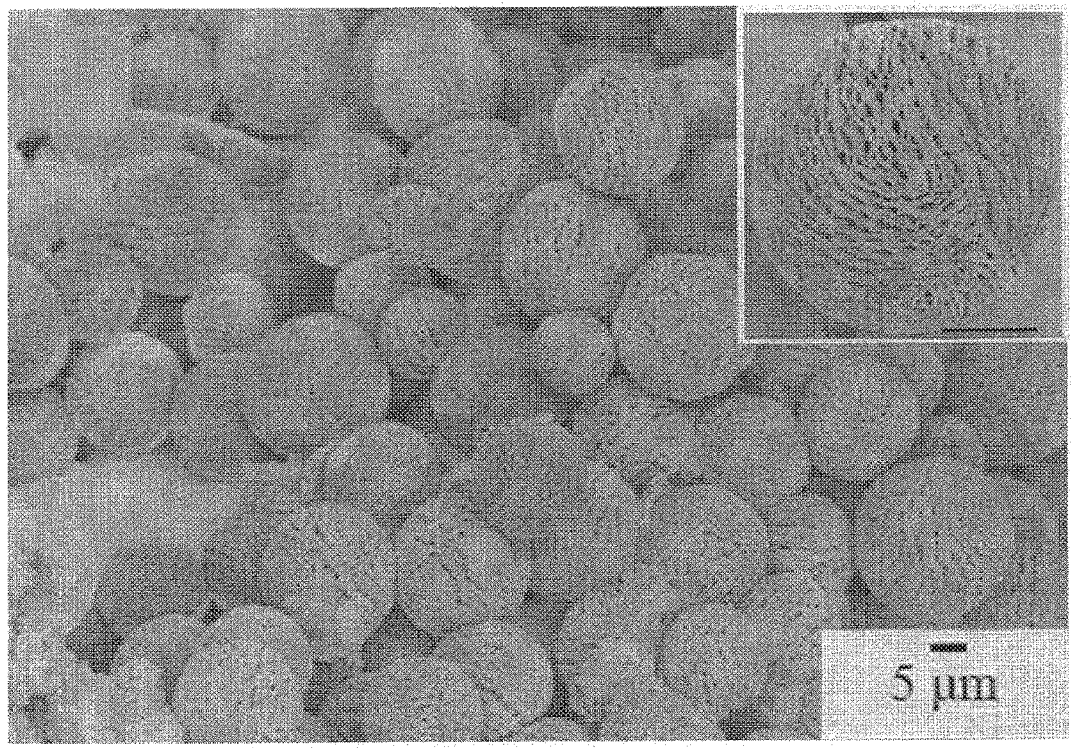
FIG. 7 is a SEM photograph of porous particles of Application Example 1-1.

FIG. 7 is a SEM photograph of porous particles of Application Example 1-1. The specific surface area of the particles measured using a nitrogen adsorption method (BEL-sorp mini manufactured by Bell Japan, Inc.) was 23.9 m$^2$/g and the volume-based average particle size thereof was 15.8 μm. As can be seen from the figure, the obtained particles exhibited a narrow particle size distribution having substantially uniform particle sizes, and the standard deviation of the distribution was 2.7 μm.

Application Example 1-2

Porous particles of Application Example 1-2 were produced in the same manner as in Application Example 1-1, except that the phospholipid solution was cooled to −20° C. and held at that temperature for 24 hours, and a precipitate was produced.

Figure 8:
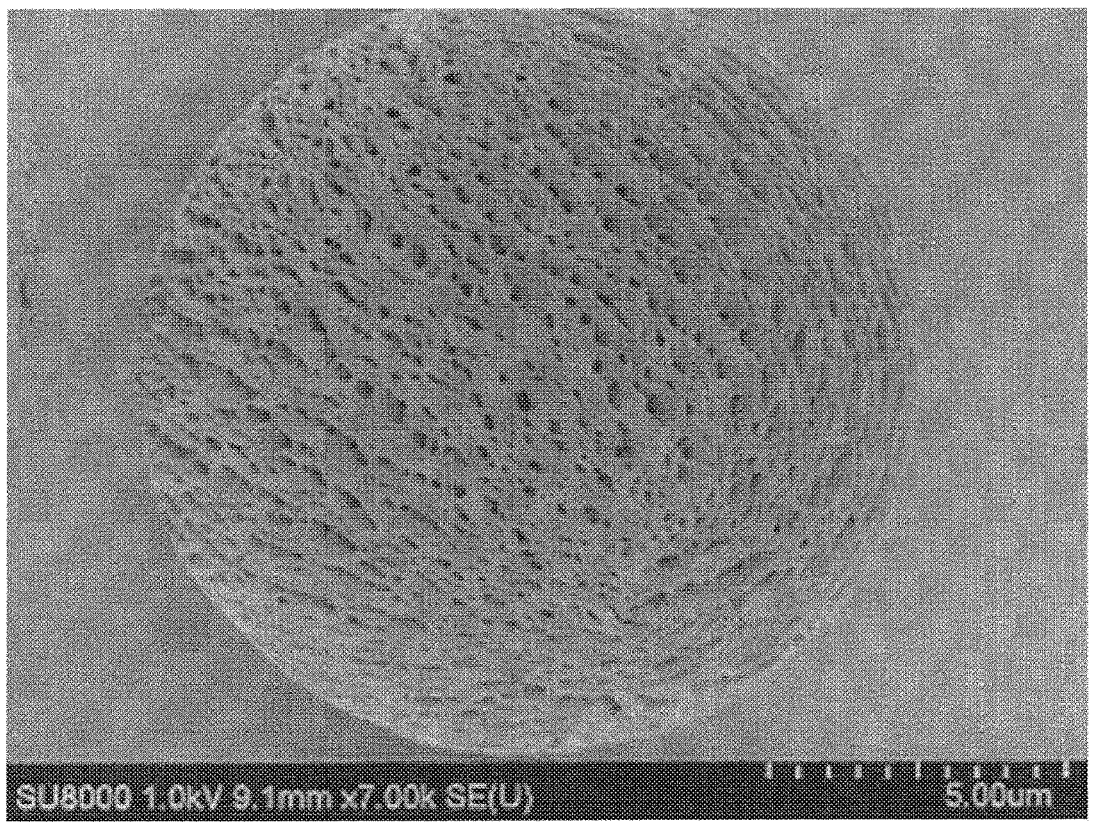
FIG. 8 is a SEM photograph of a porous particle of Application Example 1-2.

FIG. 8 is a SEM photograph of a porous particle of Application Example 1-2. The specific surface area was 6.73 m$^2$/g and the average particle size was 8.2 μm (standard deviation 1.2 μm).

Application Example 1-3

Porous particles of Application Example 1-3 were produced in the same manner as in Application Example 1-1, except that a phospholipid solution was prepared using a 3.0 wt % hydrogenated soybean lecithin solution.

Figure 9:
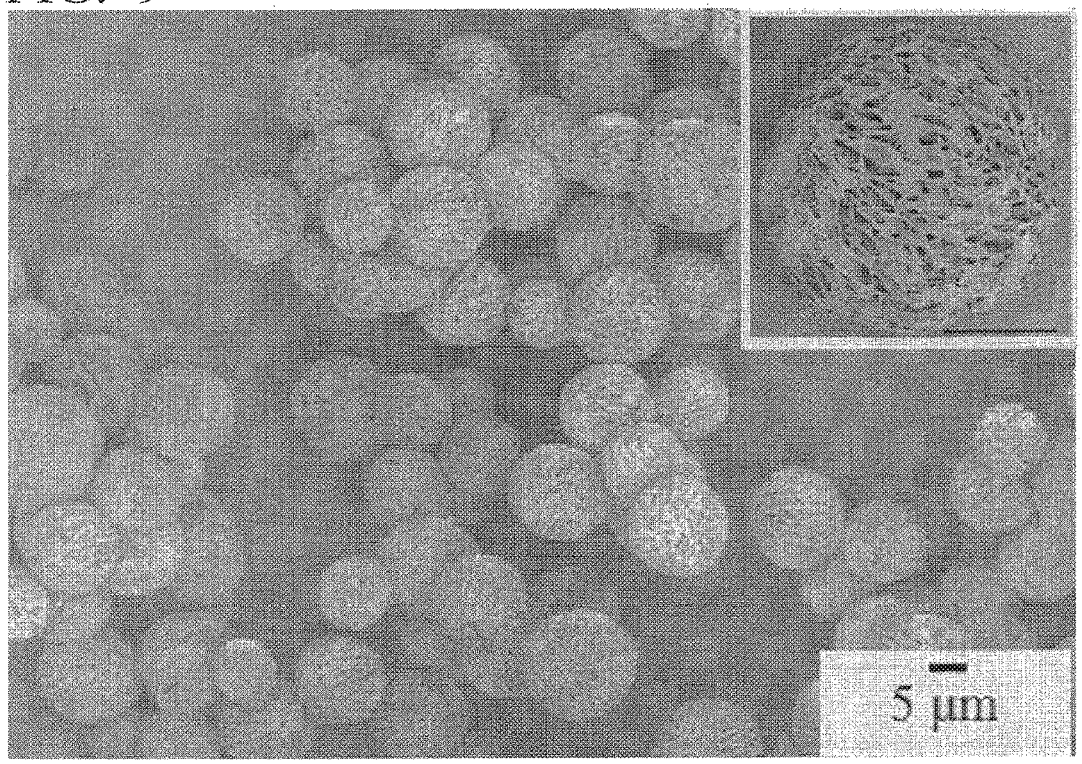
FIG. 9 is a SEM photograph of porous particles of Application Example 1-3.

FIG. 9 is a SEM photograph of porous particles of Application Example 1-3. The specific surface area was 19.8 m$^2$/g, and the average particle size was 11.5 μm (standard deviation 1.6 μm).

Application Example 1-4

Porous particles of Application Example 1-4 were produced in the same manner as in Application Example 1-1, except that a phospholipid solution was prepared using a 6.0 wt % hydrogenated soybean lecithin solution.

Figure 10:
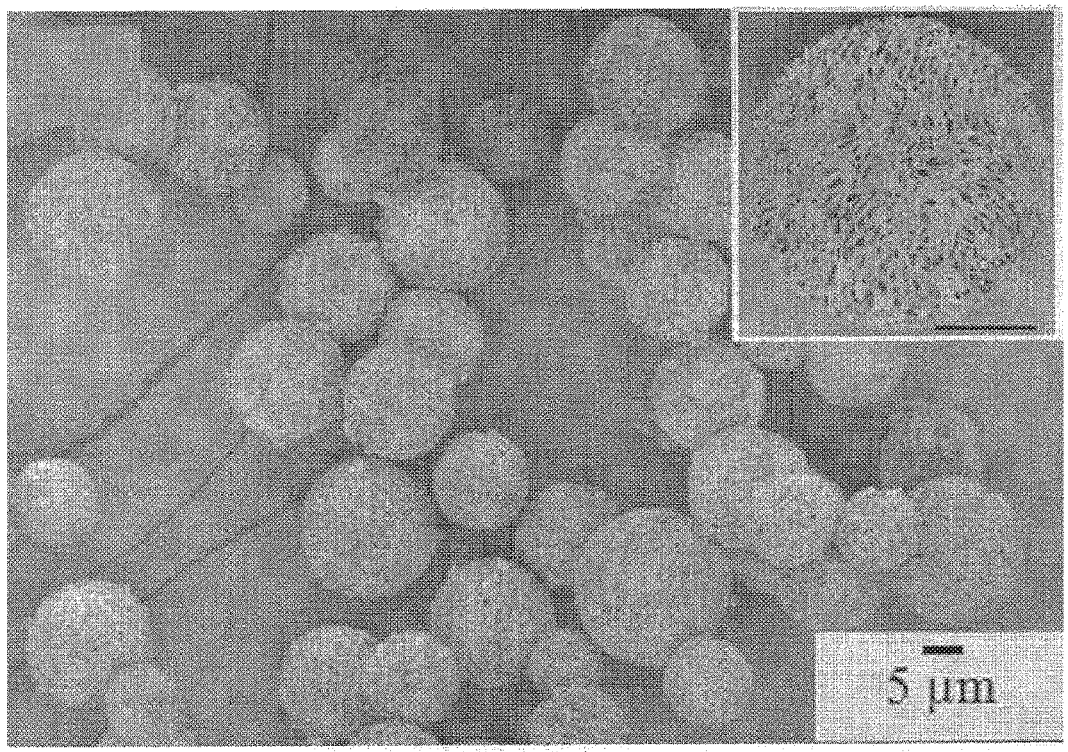
FIG. 10 is a SEM photograph of porous particles of Application Example 1-4.
Figure 11:
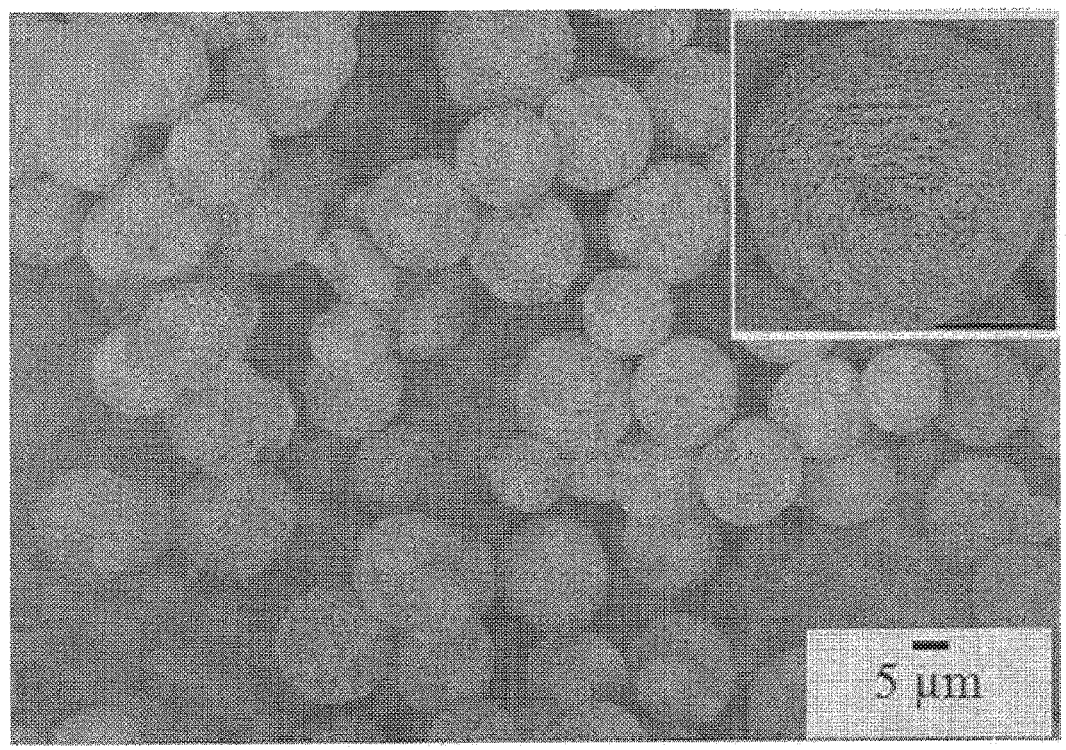
FIG. 11 is a SEM photograph of the porous particles of Application Example 1-4.

FIGS. 10 and 11 are SEM photographs of porous particles of Application Example 1-4. The specific surface area was 43.1 m$^2$/g, and the average particle size was 12.4 μm (standard deviation 1.8 μm).

Application Example 1-5

Porous particles of Application Example 1-5 were produced in the same manner as in Application Example 1-1, except that a phospholipid solution was prepared using a 6.0 wt % hydrogenated soybean lecithin solution and a mixed solvent of t-butanol:cyclohexane=2:1 was used as a mixed solvent.

Figure 12:
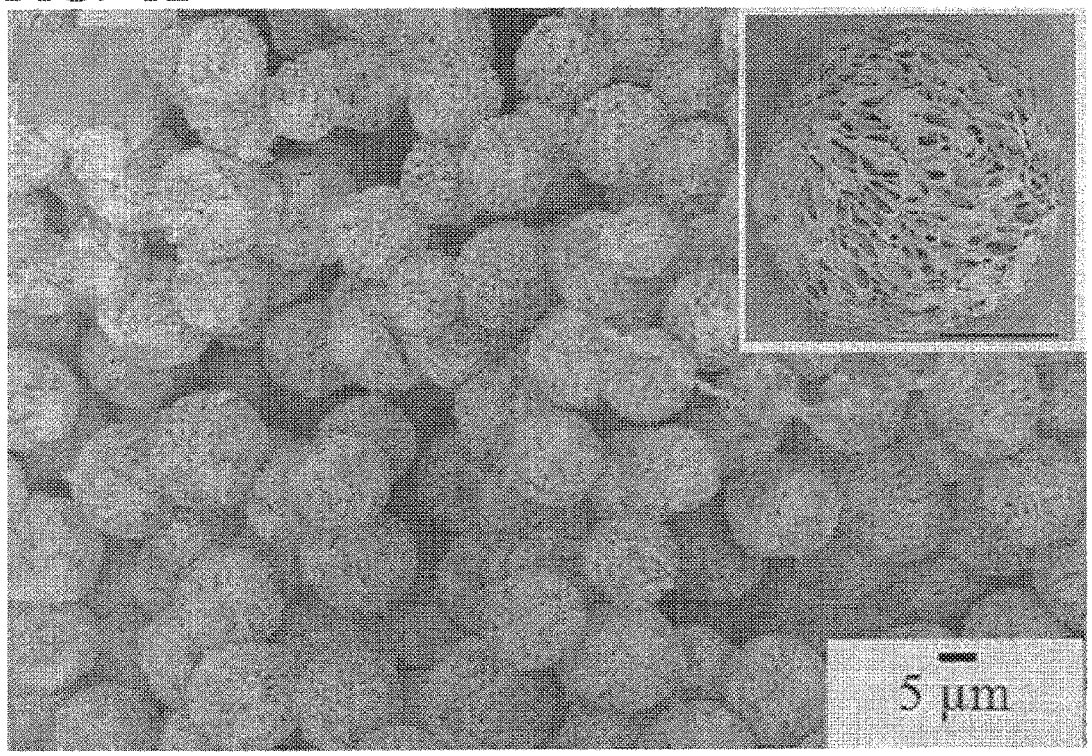
FIG. 12 is a SEM photograph of porous particles of Application Example 1-5.

FIG. 12 is a SEM photograph of porous particles of Application Example 1-5. The specific surface area was 49.3 m$^2$/g, and the average particle size was 13.0 μm (standard deviation 1.8 μm).

Application Example 1-6

Porous particles of Application Example 1-6 were produced in the same manner as in Application Example 1-1, except that a phospholipid solution was prepared using a 6.0 wt % hydrogenated soybean lecithin solution and a mixed solvent of t-butanol:cyclohexane=1:1 was used as a mixed solvent.

Figure 13:
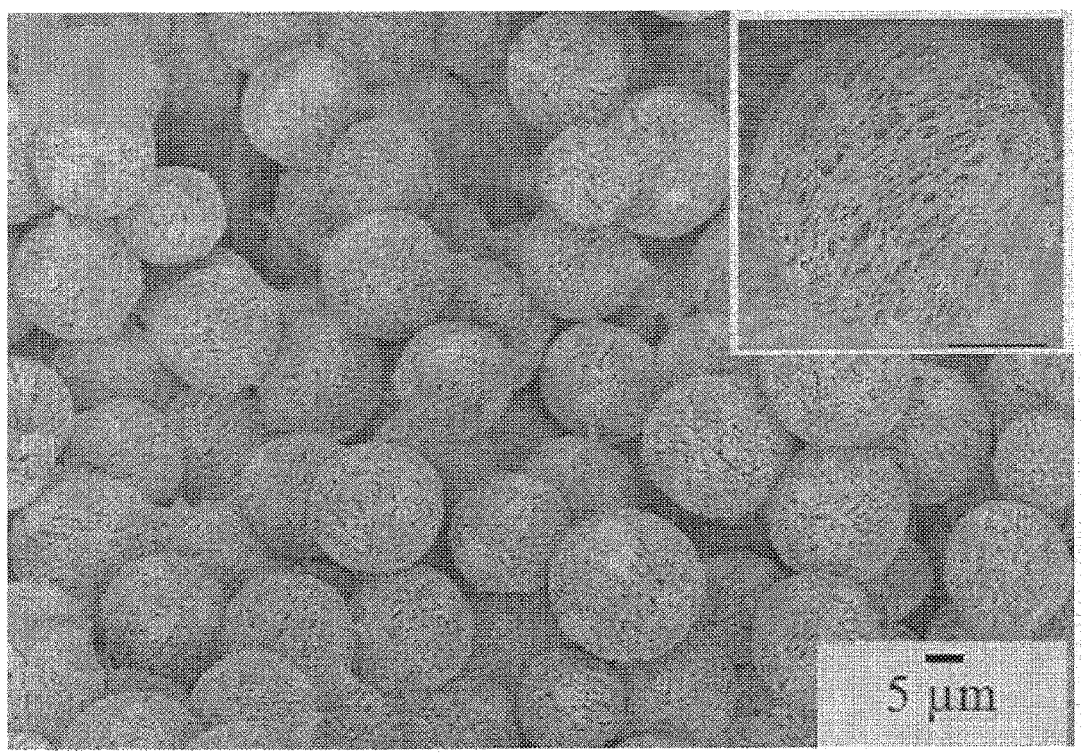
FIG. 13 is a SEM photograph of porous particles of Application Example 1-6.

FIG. 13 is a SEM photograph of porous particles of Application Example 1-6. The specific surface area was 50.4 m$^2$/g, and the average particle size was 15.6 μm (standard deviation 1.7 μm).

Application Example 1-7

Porous particles of Application Example 1-7 were produced in the same manner as in Application Example 1-1, except that a phospholipid solution was prepared using a 6.0 wt % hydrogenated soybean lecithin solution and a mixed solvent of t-butanol:cyclohexane=1:4 was used as a mixed solvent.

Figure 14:
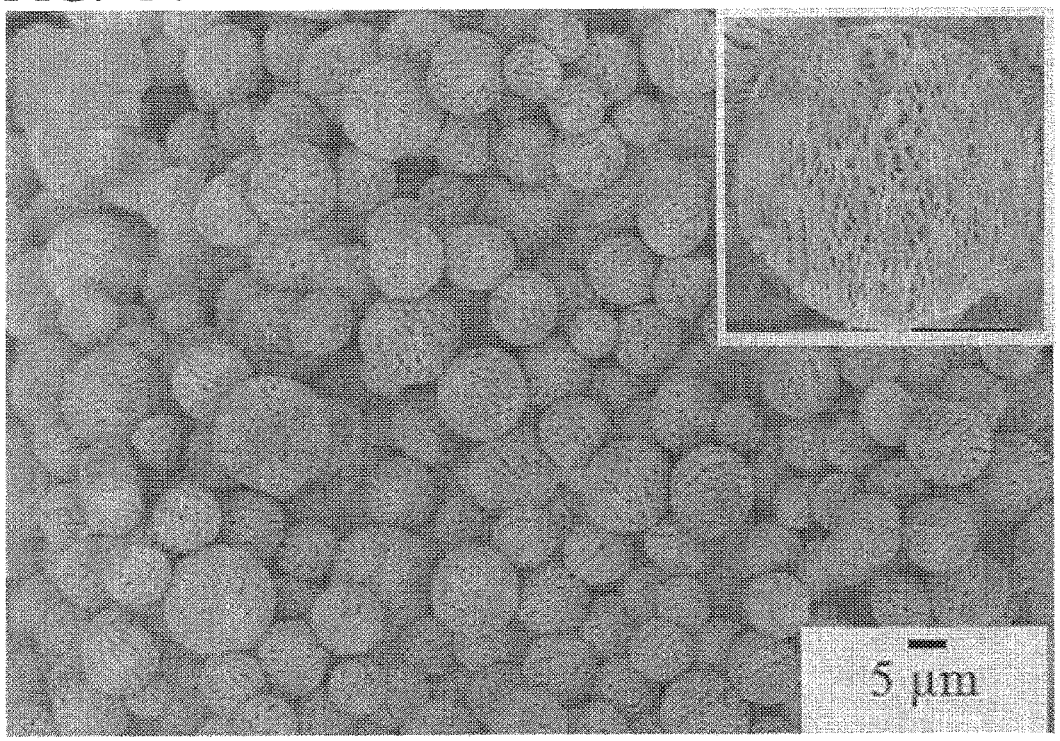
FIG. 14 is a SEM photograph of porous particles of Application Example 1-7.

FIG. 14 is a SEM photograph of porous particles of Application Example 1-7. The specific surface area was 41.7 m$^2$/g, and the average particle size was 9.9 μm (standard deviation 2.4 μm).

Application Example 1-8

Porous particles of Application Example 1-8 were produced in the same manner as in Application Example 1-1, except that the phospholipid solution was cooled to 4° C. and held at that temperature, and a precipitate was produced.

Figure 15:
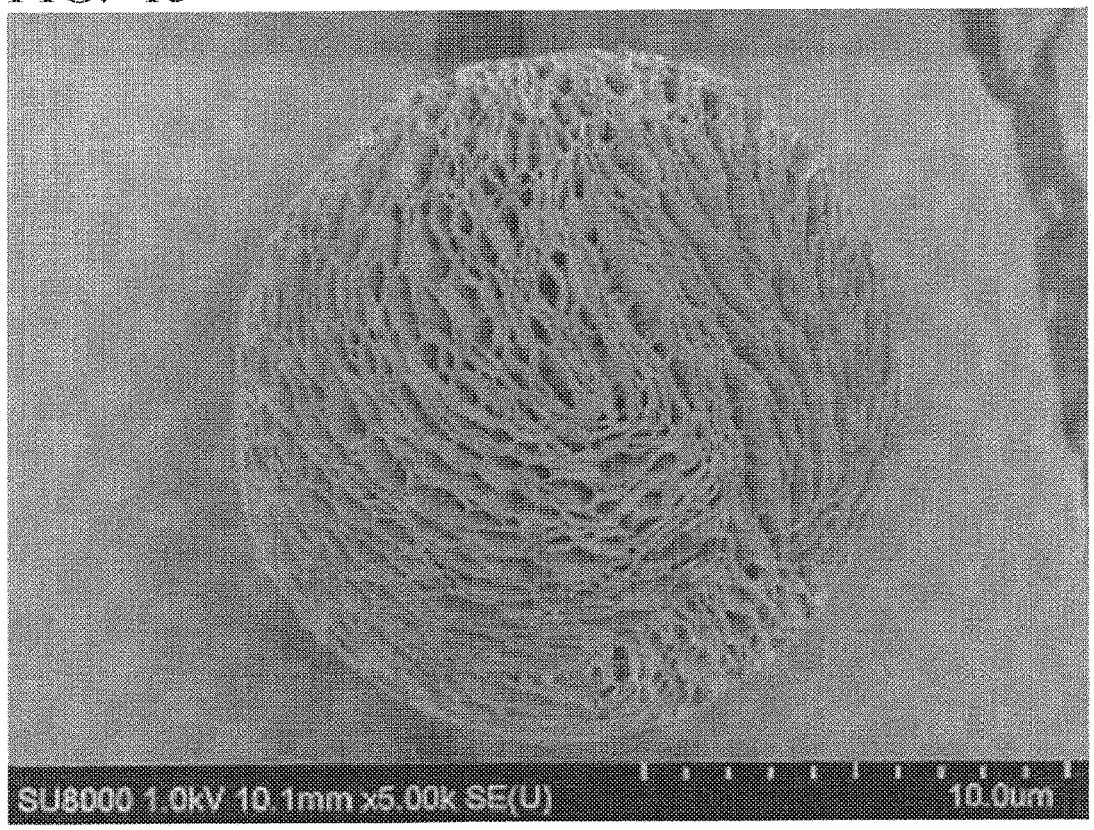
FIG. 15 is a SEM photograph of a porous particle of Application Example 1-8.

FIG. 15 is a SEM photograph of a porous particle of Application Example 1-8.

Application Example 1-9

Porous particles of Application Example 1-9 were produced in the same manner as in Application Example 1-1, except that distearoyl phosphatidylcholine and dipalmitoyl phosphatidylcholine were mixed in a molar ratio of 1:1 to uniformly dissolve in mixed solvent of t-butanol:cyclohexane=1:2 at a total concentration of 3.9 wt %, were cooled to 4° C., and thereafter held at that temperature, and a precipitate was produced.

Figure 16:
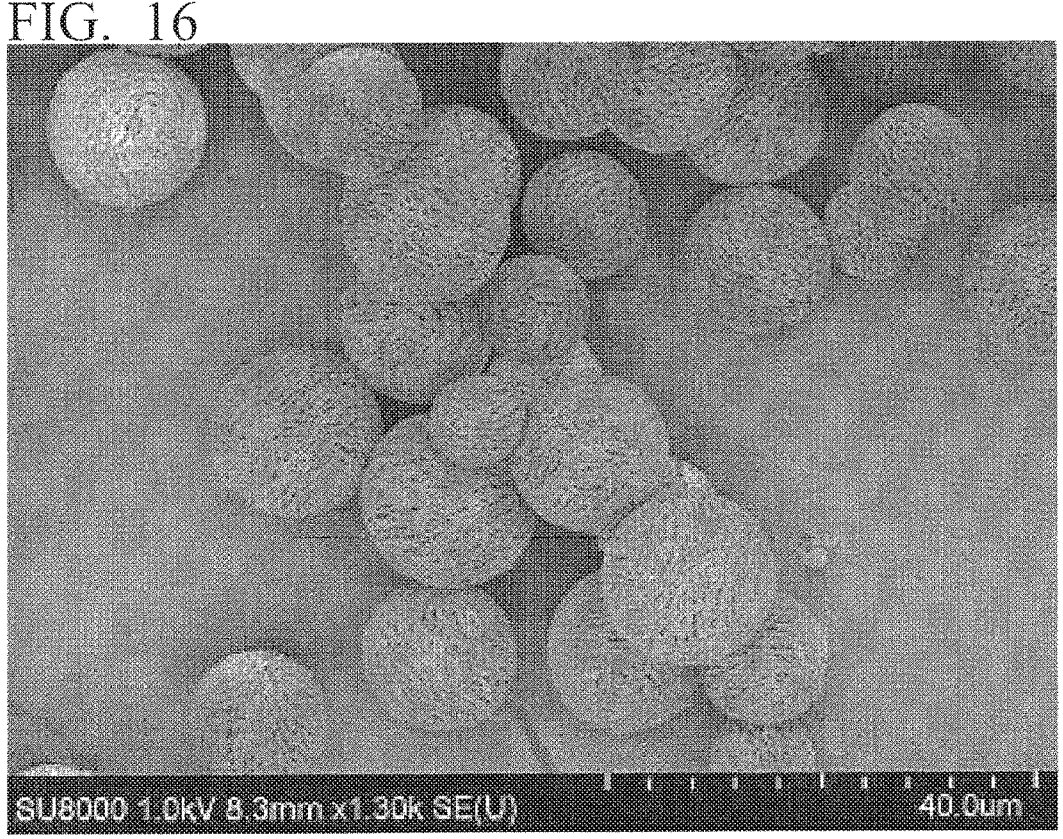
FIG. 16 is a SEM photograph of porous particles of Application Example 1-9.

FIG. 16 is a SEM photograph of porous particles of Application Example 1-9.

<Analysis Result of Micropore Distribution>

Figure 17:
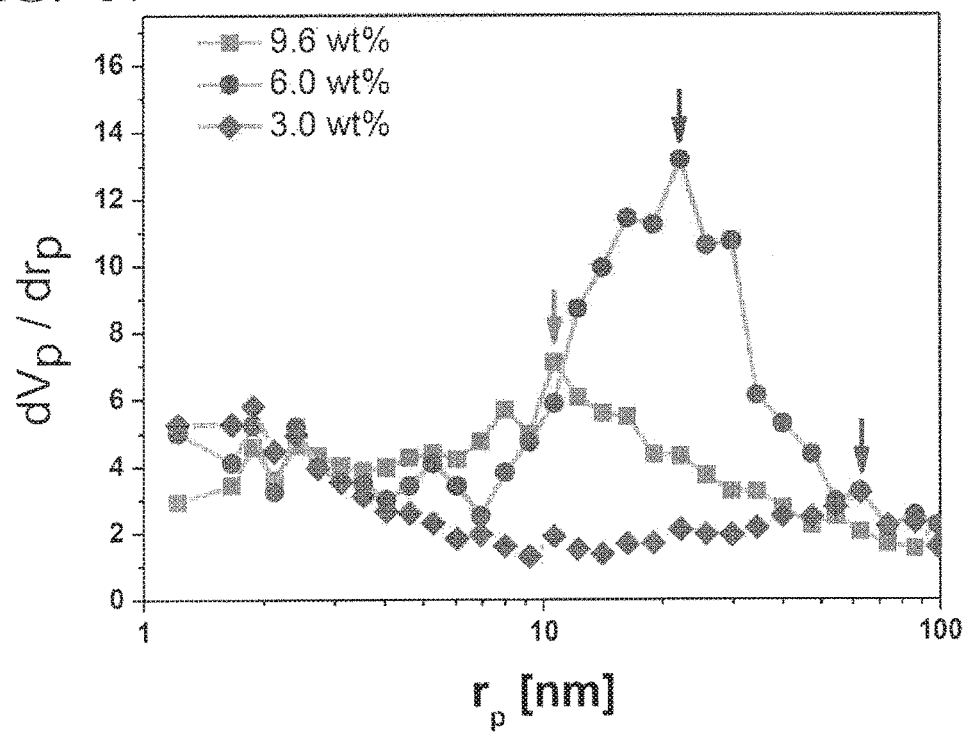
FIG. 17 is a graph (Vp: micropore volume of entire particle) illustrating a volume distribution of rp (pore size of porous particles) as an analysis result of micropore distribution for 3.0 wt % (Application Example 1-1), 9.6 wt % (Application Example 1-3), and 6.0 wt % (Application Example 1-4).

FIG. 17 is a graph illustrating relationship of Vp (total pore volume of the porous particles) to rp (pore size of the porous particles) as an analysis result of micropore distribution obtained by nitrogen adsorption method (BEL-sorp mini manufactured by Bell Japan, Inc.) for lecithin concentration 9.6 wt % (Application Example 1-1), 3.0 wt % (Application Example 1-3), and 6.0 wt % (Application Example 1-4). The vertical axis illustrates dVp/drp. That is, this figure illustrates the distribution of the pore size.

In 3.0 wt % (Application Example 1-3), clear peak was not observed, and it was considered that there were few micropores of 100 nm or less.

In 9.6 wt % (Application Example 1-1), a peak was observed in the vicinity of 10 nm.

In 6.0 wt % (Application Example 1-4), a peak was observed in the vicinity of 20 nm.

Table 1 illustrates the production conditions of the porous particles, and the specific surface area and average particle size of the obtained porous particles.

TABLE 1

| | Application Example 1-1 | Application Example 1-2 | Application Example 1-3 | Application Example 1-4 | Application Example 1-5 | Application Example 1-6 | Application Example 1-7 | Application Example 1-8 | Application Example 1-9 |
|---|---|---|---|---|---|---|---|---|---|
| Lecithin concentration (wt %) | 9.6 | 9.6 | 3 | 6 | 6 | 6 | 6 | 9.6 | — |
| Mixture concentration (wt %) of molar ratio 1:1 of distearoylphosphatidylcholine and dipalmitoylphosphatidylcholine | — | — | — | — | — | — | — | — | 3.9 |
| t-butanol:cyclohexane ratio | 1:2 | 1:2 | 1:2 | 1:2 | 2:1 | 1:1 | 1:4 | 1:2 | 1:2 |
| Precipitation temperature (° C.) | 0 | −20 | 0 | 0 | 0 | 0 | 0 | 4 | 4 |
| Specific surface area (m²/g) | 23.9 | 6.73 | 19.8 | 43.1 | 49.3 | 50.4 | 41.7 | — | — |
| Average particle size (μm) | 15.8 | 8.2 | 11.5 | 12.4 | 13 | 15.6 | 9.9 | — | — |

Application Example 2-1

A solution containing 9.2 wt % of hydrogenated soybean lecithin was prepared using a mixed solution of t-butanol:cyclohexane=1:2 as a solvent.

Next, this solution was held at 4° C. for 1 day to obtain a precipitate.

Next, the precipitate was frozen with liquid nitrogen and thereafter freeze-dried.

In this manner, porous particles of Application Example 2-1 were obtained.

Lamellar layer intervals (hereinafter referred to as "lamellar interval") obtained by small angle X-ray scattering were 6.17 nm.

Application Example 2-2

A 9.2 wt % hydrogenated soybean lecithin solution was prepared using a mixed solution of t-butanol:cyclohexane=1:2 as a solvent. Separately, a 20 wt % aqueous glucose solution was prepared and added so as to be 4.6 wt % to a lecithin solution, so that a lecithin solution containing glucose was prepared. Porous particles of Application Example 2-2 were obtained in the same manner as in Application Example 2-1, after the precipitation operation.

Figure 18:
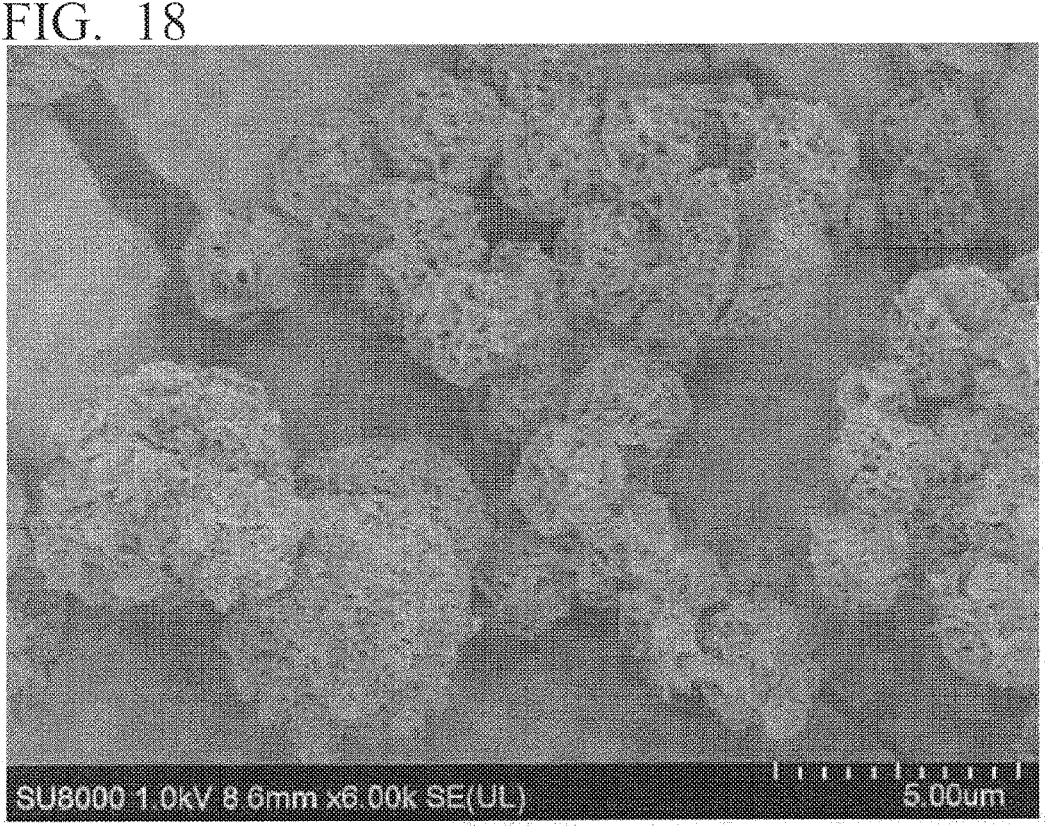
FIG. 18 is a SEM photograph of porous particles of Application Example 2-2.

FIG. 18 is a SEM photograph of porous particles of Application Example 2-2.

The lamellar interval obtained by small angle X-ray scattering was 6.35 nm.

Application Example 2-3

Porous particles of Application Example 2-3 were obtained in the same manner as in Application Example 2-2, except that the aqueous glucose solution concentration was 40 wt %.

Figure 19:
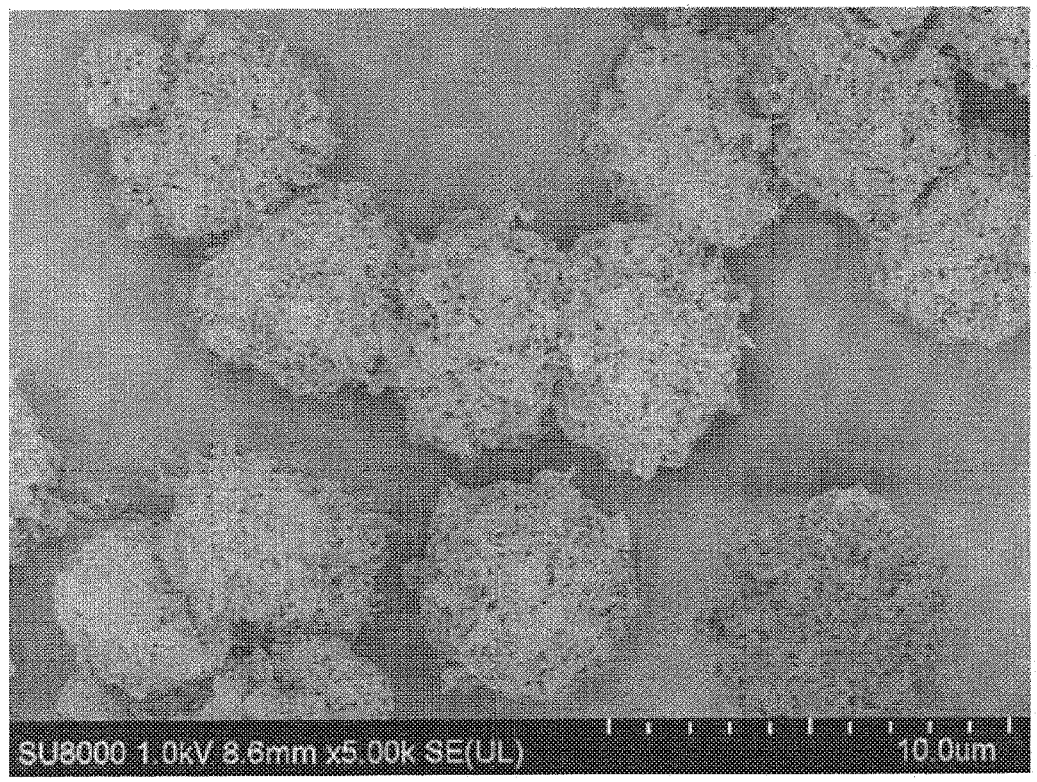
FIG. 19 is a SEM photograph of porous particles of Application Example 2-3.

FIG. 19 is a SEM photograph of porous particles of Application Example 2-3.

The lamellar interval obtained by small angle X-ray scattering was 6.59 nm.

Application Example 2-4

Porous particles of Application Example 2-4 were obtained in the same manner as in Application Example 2-2, except that the aqueous glucose solution concentration was 60 wt %.

Figure 20:
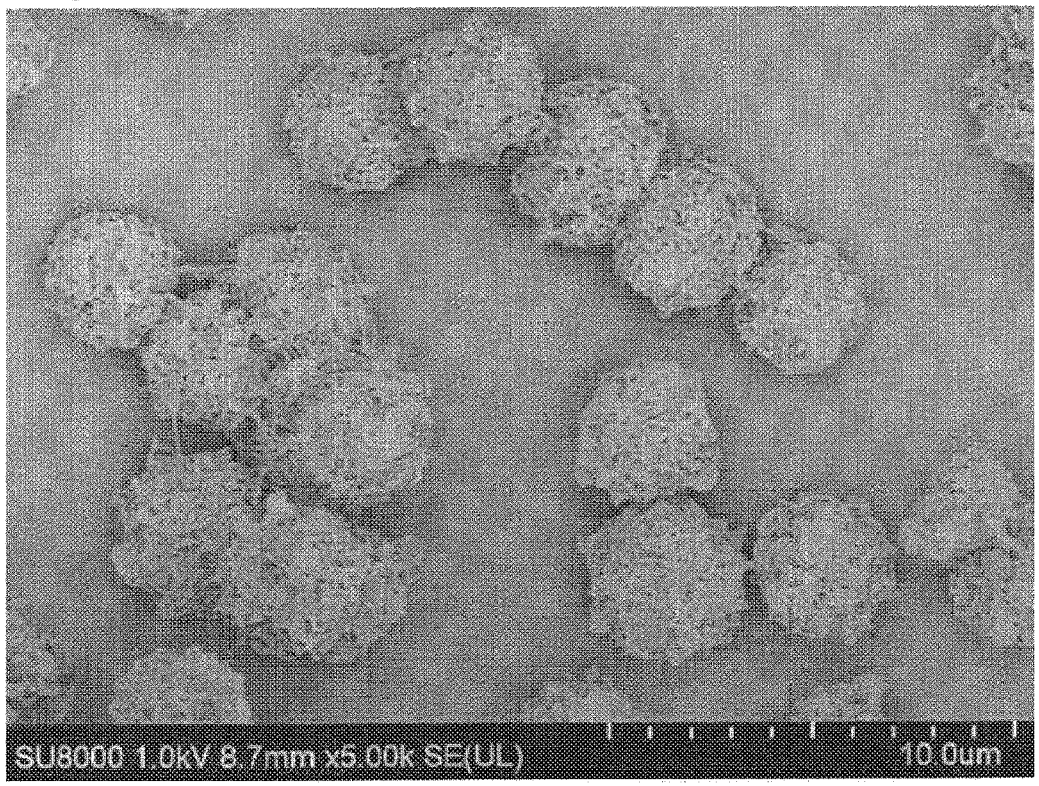
FIG. 20 is a SEM photograph of porous particles of Application Example 2-4.

FIG. 20 is a SEM photograph of porous particles of Application Example 2-4.

The lamellar interval obtained by small angle X-ray scattering was 6.74 nm.

Application Example 2-5

Porous particles of Application Example 2-5 were obtained in the same manner as in Application Example 2-2, except that the aqueous glucose solution concentration was 80 wt %.

Figure 21:
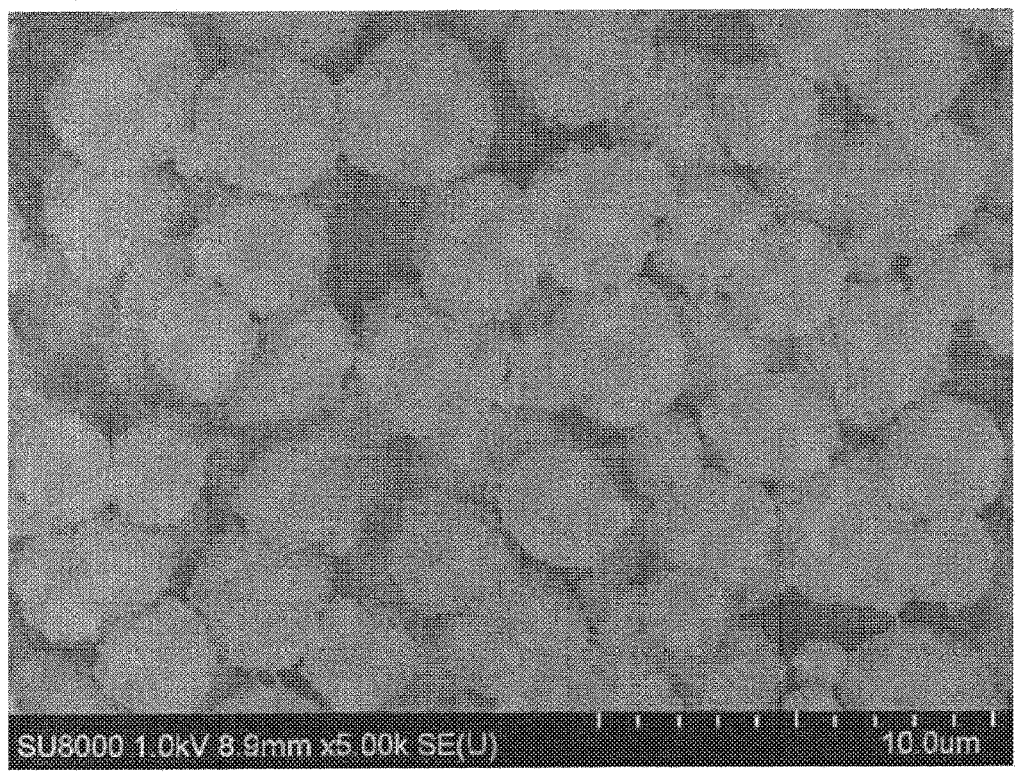
FIG. 21 is a SEM photograph of porous particles of Application Example 2-5.

FIG. 21 is a SEM photograph of porous particles of Application Example 2-5.

The lamellar interval obtained by small angle X-ray scattering was 6.84 nm.

Table 2 summarizes the results of production conditions and lamellar intervals.

TABLE 2

|  | Application Example 2-1 | Application Example 2-2 | Application Example 2-3 | Application Example 2-4 | Application Example 2-5 |
|---|---|---|---|---|---|
| Lecithin concentration (wt %) | 9.2 | 9.2 | 9.2 | 9.2 | 9.2 |
| t-butanol:cyclohexane ratio | 1:2 | 1:2 | 1:2 | 1:2 | 1:2 |
| Added aqueous glucose solution concentration (wt %) | 0 | 20 | 40 | 60 | 80 |
| Precipitation temperature (° C.) | 4 | 4 | 4 | 4 | 4 |
| Lamellar interval (nm) | 6.17 | 6.35 | 6.59 | 6.74 | 6.84 |

The lamellar intervals widened as the concentration of the added aqueous glucose solution increased. These are considered due to (1) the glucose mainly exists between the lipid bilayer membranes and (2) an increase in the amount of glucose existing between the lipid bilayer membranes with an increase in glucose concentration, and an increase in distance between the lipid bilayer membranes.

Application Example 3

(Production of Porous Particles Containing Dextran)

A 9.6 wt % hydrogenated soybean lecithin solution was prepared using a mixed solution of t-butanol:cyclohexane=1:2. Subsequently, a 0.1 wt % of dextran modified with fluorescein isocyanate (hereinafter referred to as "FITC dextran") was added so that dextran/lecithin=0.5 μg/200 mg or 0.5 μg/100 mg.

Next, the hydrogenated soybean lecithin solution was held at 4° C. for 1 day to produce a precipitate.

Next, the precipitate was frozen with liquid nitrogen, and thereafter was freeze-dried to produce the porous particles containing FITC dextran of Application Example 3.

(FITC Dextran Release Experiment)

Application Example 3-1

The porous particles containing FITC dextran (dextran/lecithin=0.5 μg/200 mg) of Application Example 3 were dispersed in a phosphate buffer solution of pH 7 at 200 mg/100 mL.

Next, the solution was collected over time, filtration by a filter and a fluorescence analysis of a filtrate were performed, and the concentration of FITC dextran was measured.

Application Example 3-2

The FITC dextran concentration in the solution was measured in the same manner as in Application Example 3-1, except that the porous particles containing FITC dextran (dextran/lecithin=0.5 μg/100 mg) of Application Example 3 were dispersed at 100 mg/100 mL.

Figure 22:
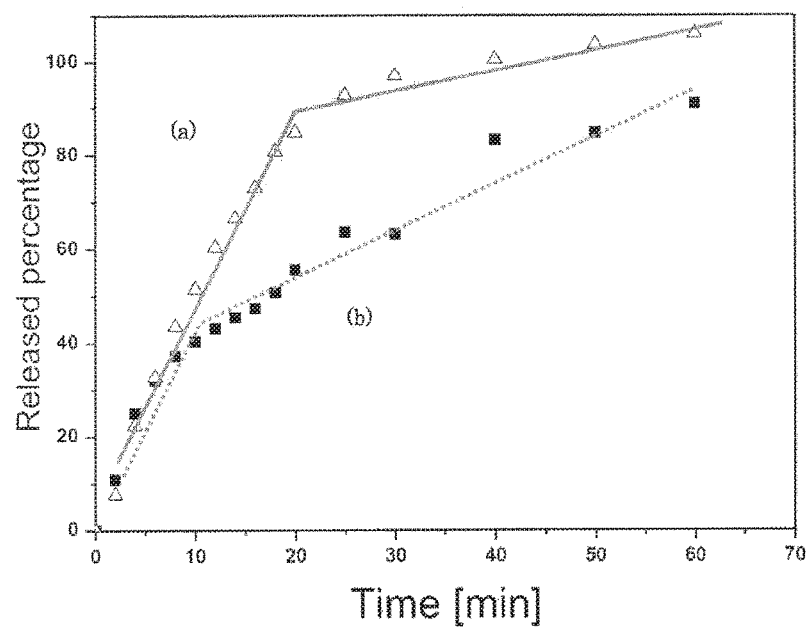
FIG. 22 is a graph illustrating the relationship between the release percentage of FITC dextran from the porous particles of Example 3 containing the FITC dextran and the elapsed time and is Application Example 3-1(b) and Application Example 3-2(a).

FIG. 22 is a graph illustrating the relationship between the release percentage of FITC dextran from the porous particles of Application Example 3 containing the FITC dextran and the time elapsed, and is Application Example 3-1(b) and Application Example 3-2(a).

In both cases, biphasic release behavior was observed. This is considered due to the fact that FITC dextran captured between lamellae is less likely to be released from FITC dextran captured in the pores.

In this manner, it was disclosed that the porous particles obtained by the method of the present invention act as a carrier capable of controlling the release rate.

Table 3 summarizes the results of production conditions and release characteristics.

TABLE 3

|  | Application Example 3 |  |
|---|---|---|
| Lecithin concentration (wt %) | 9.6 | |
| t-butanol:cyclohexane ratio | 1:2 | |
| Precipitation temperature (° C.) | 4 | |
|  | Application Example 3-1 | Application Example 3-2 |
| FITC dextran concentration | 0.5 μg/200 mg | 0.5 μg/100 mg |
| Particle amount/phosphate buffer liquid volume of pH 7 | 200 mg/100 mL | 100 mg/100 mL |
| Released FITC dextran concentration (%) @ 60 h | 80 | 100 |

(Production of Porous Particles Containing Theophylline)

Application Example 4-1

A 9.2 wt % hydrogenated soybean lecithin solution was prepared using a mixed solution of t-butanol:cyclohexane=1:2. Subsequently, a 0.25 wt % aqueous theophylline solution was prepared, and a 4.6 wt % aqueous theophylline solution was added to the lecithin solution.

Next, the hydrogenated soybean lecithin solution was held at 4° C. for 1 day to prepare a precipitate.

Next, the precipitate was frozen with liquid nitrogen, and thereafter was freeze-dried to obtain the porous particle containing theophylline of Application Example 4-1.

Figure 23:
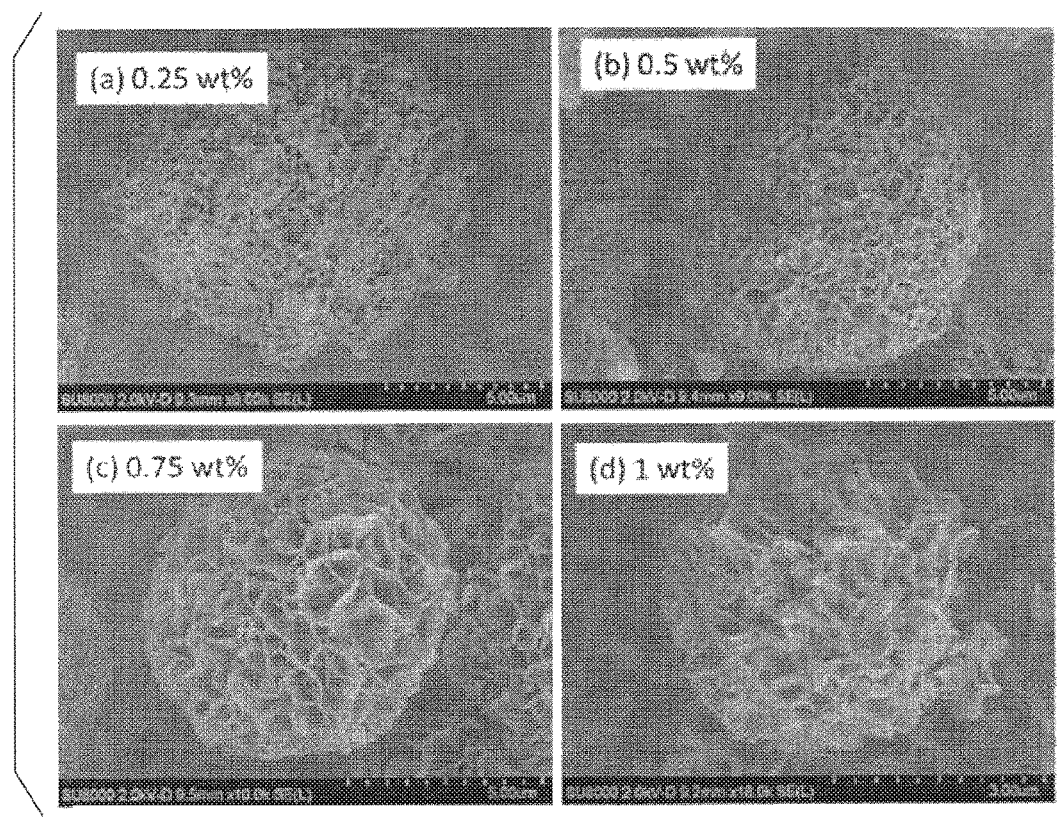
FIG. 23 is a SEM photograph of porous particles and is Application Example 4-1(a), Application Example 4-2(b), Application Example 4-3(c), and Application Example 4-4 (d).

FIG. 23(a) is a SEM photograph of porous particles of Application Example 4-1.

Application Example 4-2

Porous particles containing theophylline of Application Example 4-2 were obtained in the same manner as in Application Example 4-1, except that the concentration of the added 4.6 wt % aqueous theophylline solution was doubled.

FIG. 23(b) is a SEM photograph of porous particles of Application Example 4-2.

Application Example 4-3

Porous particles containing theophylline of Application Example 4-3 were obtained in the same manner as in Application Example 4-1, except that the concentration of the added 4.6 wt % aqueous theophylline solution was tripled.

FIG. 23(c) is a SEM photograph of porous particles of Application Example 4-3.

Application Example 4-4

Porous particles containing theophylline of Application Example 4-4 were obtained in the same manner as in Application Example 4-1, except that the concentration of the added 4.6 wt % aqueous theophylline solution was quadrupled.

FIG. 23(d) is a SEM photograph of porous particles of Application Example 4-4.

(Theophylline Release Experiment)

First, the porous particles containing theophylline of Application Examples of 4-1 to 4-4 were dispersed in a phosphate buffer solution of pH 7 at 200 mg/100 mL.

Next, the solution was collected over time, filtered by a filter, and thereafter analyzed by high-performance liquid chromatography, and the concentration of theophylline in the solution was measured.

Figure 24:
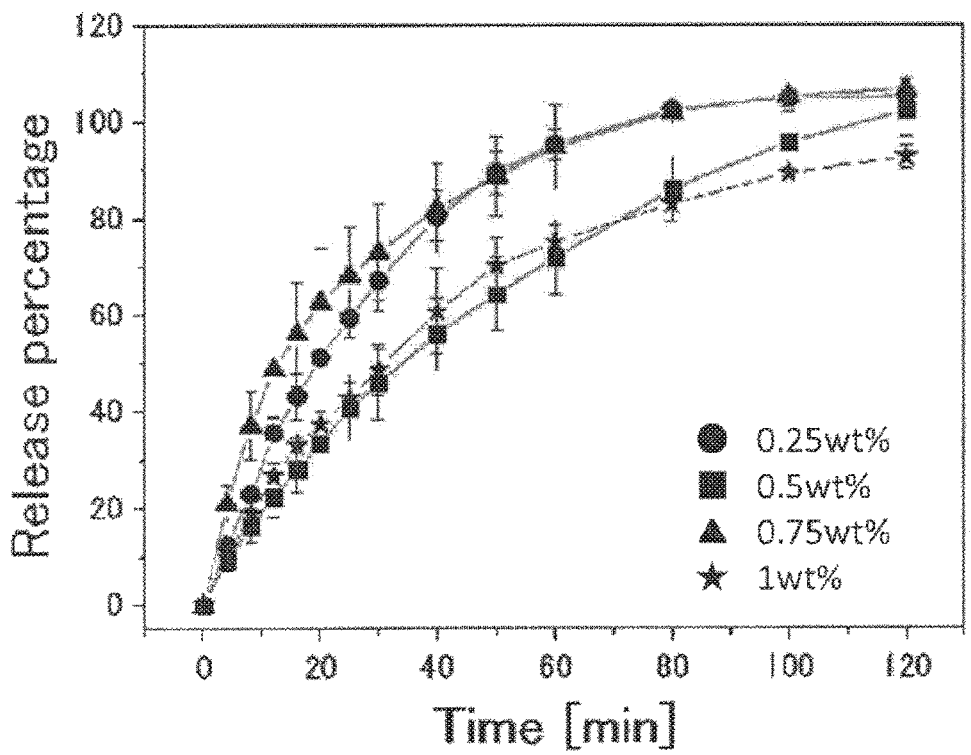
FIG. 24 is a graph illustrating the relationship between the release percentages of theophylline from the porous particles containing theophylline of Application Examples 4-1 to 4-4 and the time elapsed.

FIG. 24 is a graph illustrating the relationship between the release percentages of theophylline from the porous particles containing theophylline of Application Examples 4-1 to 4-4 and the time elapsed.

From the porous particles containing theophylline of Application Examples 4-1 to 4-4, the theophylline was gradually released with time.

Compared with the fact that the whole amount was dissolved instantaneously with theophylline alone, it was confirmed that theophylline was included in the porous particles containing theophylline of Application Examples 4-1 to 4-4, and that the contained theophylline was gradually released.

Table 4 summarizes the results of production conditions and release characteristics.

TABLE 4

|  |  | Application Example 4-1 | Application Example 4-2 | Application Example 4-3 | Application Example 4-4 |
|---|---|---|---|---|---|
| Lecithin concentration (wt %) | | 9.6 | 9.6 | 9.6 | 9.6 |
| Solvent | t-butanol:cyclohexane (ratio) | 1:2 | 1:2 | 1:2 | 1:2 |
| Other solvent | 4.6 wt % aqueous theophylline solution concentration (wt %) | 0.25 | 0.5 | 0.75 | 1 |
| Precipitation temperature (° C.) | | 4 | 4 | 4 | 4 |
| Spherical particles | | Produced | Produced | Produced | Produced |
| Particle amount/volume of pH 7 phosphate buffer | | 200 mg/100 mL | 200 mg/100 mL | 200 mg/100 mL | 200 mg/100 mL |
| Released theophylline concentration (%) @ 60 h | | 85 | 70 | 85 | 73 |
| Released theophylline concentration (%) @ 120 h | | 100 | 98 | 100 | 83 |

Reference Example 1

The hydrogenated soybean lecithin was dissolved in t-butanol at 9.6 wt % and thereafter freeze-dried.

Figure 25:
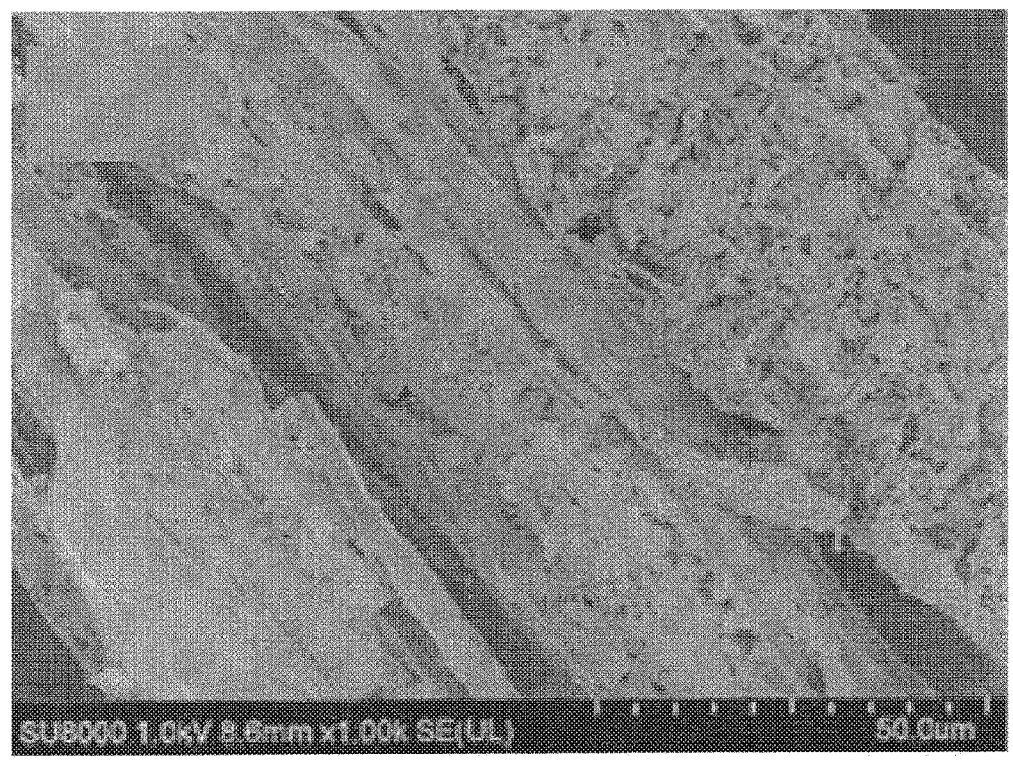
FIG. 25 is a SEM photograph of a bulk body of Comparative Example 1.

A bulk body as illustrated in the SEM photograph of FIG. 25 was obtained and spherical particles could not be obtained.

Reference Example 2

A 9.6 wt % hydrogenated soybean lecithin solution was prepared using a mixed solution of t-butanol:cyclohexane=1:2.

Next, the hydrogenated soybean lecithin solution was held at 25° C. for 1 day to produce a precipitate.

Next, the precipitate was frozen with liquid nitrogen and thereafter freeze-dried.

A plate-like structure was obtained.

Spherical particles were not obtained.

Figure 26:
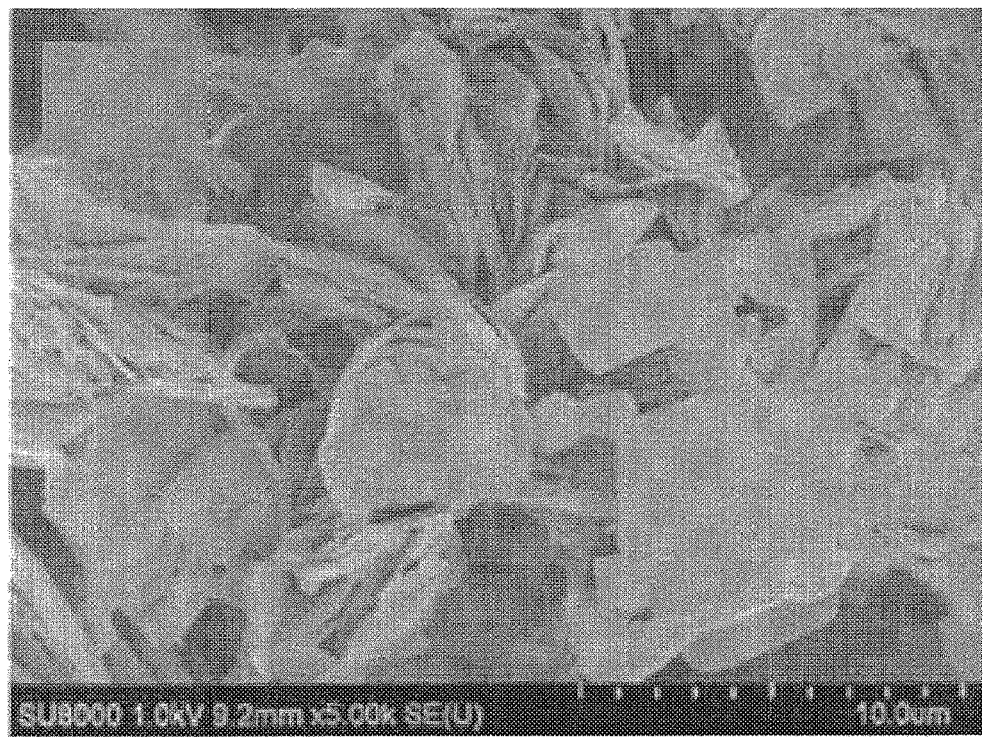
FIG. 26 is a SEM photograph of the plate-like structure of Comparative Example 2.

FIG. 26 is a SEM photograph of the plate-like structure of Comparative Example 2.

The experimental conditions and results are summarized in Table 5.

TABLE 5

|  | Reference Example 2 |
|---|---|
| Raw material | hydrogenated soybean lecithin |
| Lecithin concentration (wt %) | 9.6 |
| t-butanol:cyclohexane ratio | 1:2 |
| Precipitation temperature (° C.) | 25 |
| Spherical particles | Not produced |

Application Example 5

A solution of t-butanol:cyclohexane=1:2 containing 3.9 wt % hydrogenated soybean lecithin and 0.2 wt % prednisolone was held at 4° C. for 1 day, and thereafter the precipitate thereof was frozen with liquid nitrogen and freeze-dried, so that the porous particles were obtained.

Figure 27:
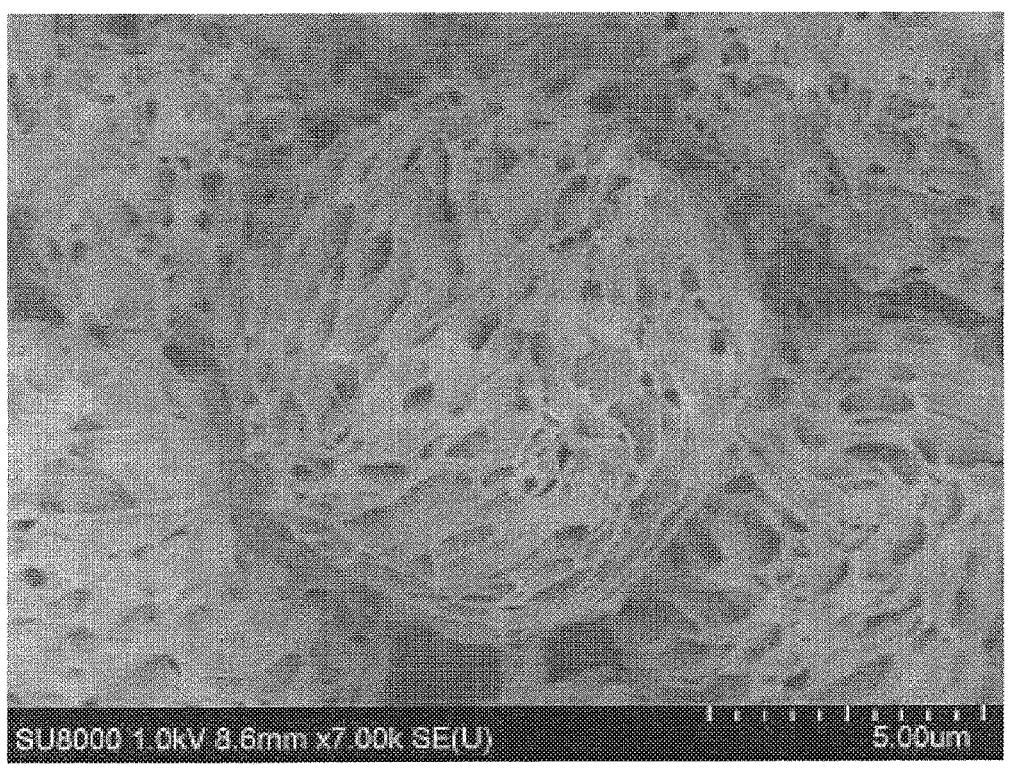
FIG. 27 is a SEM photograph of porous particles (Application Example 5).

FIG. 27 is an electron microscope photograph of the porous particles

The content of prednisolone distributed in the porous particles was 80%.

Application Example 6

Figure 28A:
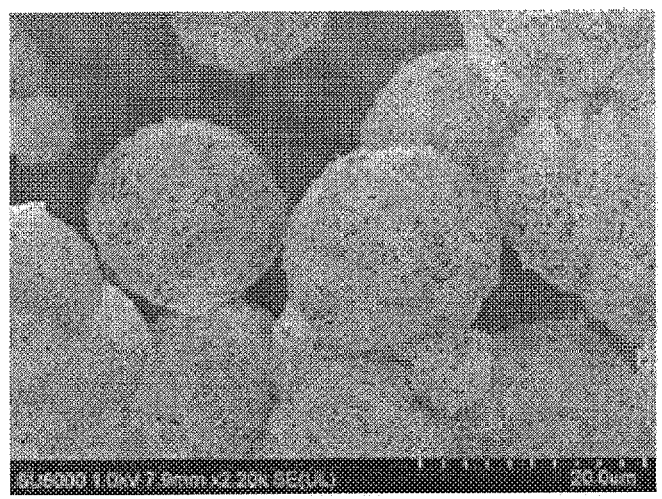
FIG. 28A is a SEM photograph of porous particles containing fenofibrate (Application Example 6).
Figure 28B:
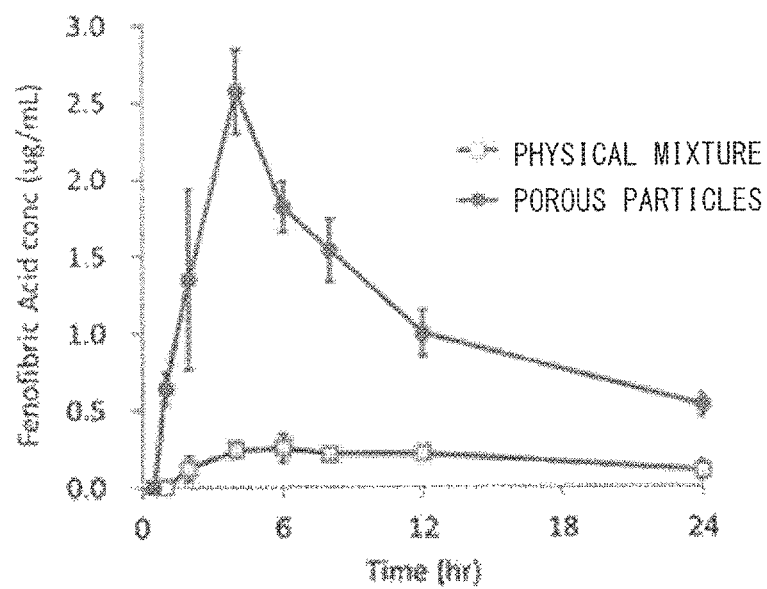
FIG. 28B is a graph illustrating blood concentrations of fenofibrate metabolite.

A solution containing 9 wt % hydrogenated soybean lecithin and 1 wt % fenofibrate was prepared using a mixed solution of t-butanol:cyclohexane=1:2. This solution was held at 4° C. for 1 day, and thereafter was frozen with liquid nitrogen and further freeze-dried, so that the porous particles containing fenofibrate were obtained. FIG. 28A illustrates an SEM photograph thereof. The obtained particles were orally administered to rats at a drug amount conversion of 7.5 mg/kg, and blood concentrations of fenofibrate metabolites were measured. For comparison, hydrogenated soybean lecithin used as a raw material for the porous particles was physically mixed with fenofibrate at a ratio of 9:1 and the same amount was administered. As illustrated in FIG. 28B, in a case where the porous particles were administered, the oral absorbability remarkably improved as compared with the administration of a physical mixture of hydrogenated soybean lecithin as a raw material and fenofibrate. It is considered that this is because the porous particles and the intestinal mucosa have affinity and the transmucosal absorbability was promoted.

INDUSTRIAL APPLICABILITY

The porous particles and the porous particles containing guest molecules obtained by the method of the present invention are provided with a porous structure and are very useful as a carrier for a guest molecule, particularly a drug molecule, for an oral, inhalable, injectable, transdermal dosage forms (including cosmetics), ophthalmic solution, and the like that make use of sustained release and low density properties.

REFERENCE SIGNS LIST

11 . . . Porous particles,
21 . . . Portion consisting only of amphiphilic molecules,
21c, 21c' . . . Pore,
23A, 23B, 23C . . . Lipid bilayer membrane,
25A, 25B . . . Lipid layer,
31A, 31A' . . . Hydrophobic layer,
31B, 31B' . . . Hydrophilic layer,
33 . . . Linking portion,
38 . . . Hydrophilic group,
39A, 39B . . . Hydrophobic group,
41 . . . Amphiphilic molecules (phospholipid),
50 . . . Guest molecules.

The invention claimed is:

1. A method for producing porous particles comprising:
(1) preparing a solution of an amphiphilic substance by dissolving the amphiphilic substance in a mixed solvent capable of being freeze-dried;
(2) producing a phase separated spherical precipitate containing the amphiphilic substance by cooling the solution obtained in (1) to a temperature equal to or less than a phase separation temperature of the solution but the temperature is such that the solution does not freeze, and thereafter holding the solution at the temperature; and
(3) producing porous particles by freeze-drying the solution containing the precipitate obtained in (2),
wherein the mixed solvent is such that phase separation is caused therein by cooling in the presence of the amphiphilic substance, and
wherein the amphiphilic substance comprises a phospholipid.

2. The production method according to claim 1,
wherein the porous particles have a lamellar structure.
3. The production method according to claim 1,
wherein the phospholipid is at least one selected from the group consisting of phosphatidylcholine, phosphatidylglycerol, phosphatidylethanolamine, phosphatidylserine, phosphatidylinositol, phosphatidic acid, sphingomyelin, and ceramide.
4. The production method according to claim 1,
wherein the phospholipid is of natural origin.
5. The production method according to claim 4,
wherein the phospholipid of natural origin is hydrogenated soybean lecithin or hydrogenated egg yolk lecithin.
6. The production method according to claim 1,
wherein the amphiphilic substance is at least one selected from the group consisting of dicetyl phosphate, dihexadecyl phosphate, dioctadecyl dimethyl ammonium salt, and stearylamine.
7. The production method according to claim 1,
wherein the mixed solvent is a mixed solvent of two or more solvents selected from the group consisting of water, t-butanol, cyclohexane, dioxane, dimethylsulfoxide, diethylamine, acetic acid, and t-amyl alcohol.
8. The production method according to claim 7,
wherein the mixed solvent further contains at least one solvent selected from the group consisting of methanol, ethanol, propanol, isopropanol, butanol, hexane, heptane, octane, isooctane, nonane, decane, dodecane, ethers, acetonitrile, acetone, chloroform, dichloromethane, dimethylformamide, dimethylacetamide, N-methylpyrrolidone, isopentane, methylamine, ethylamine, isobutane, and ethylene oxide.
9. The production method according to according to claim 1,
wherein in (1), a biocompatible substance is further dissolved.
10. The production method according to claim 1, further comprising:
(4) mixing the porous particles with a biocompatible substance.
11. The production method according to claim 9,
wherein the biocompatible substance is a medicine.
12. The production method according to claim 11,
wherein the medicine is at least one selected from the group consisting of a low molecular medicine, a peptide medicine, an antibody medicine, and a nucleic acid medicine.
13. The production method according to claim 9,
wherein the biocompatible substance is at least one selected from the group consisting of a stabilizer, a humectant, a thickener, and an excipient.
14. The production method according to claim 1,
wherein the volume average particles size of the porous particles is 100 nm or more and 50 µm or less.
15. The production method according to claim 1,
wherein the mixed solvent consists of t-butanol and cyclohexane.

* * * * *